(12) United States Patent
Lynch et al.

(10) Patent No.: US 8,303,594 B2
(45) Date of Patent: Nov. 6, 2012

(54) METHOD AND APPARATUS FOR REMOVAL OF TISSUE

(75) Inventors: Michael D. Lynch, Skaneateles, NY (US); Carlos E. Collazo, Old Greenwich, CT (US); An Chen, Lincoln Park, NJ (US); Brian Graner, Rochester, MN (US)

(73) Assignee: Howmedica Osteonics Corp., Mahwah, NJ (US)

( * ) Notice: Subject to any disclaimer, the term of this patent is extended or adjusted under 35 U.S.C. 154(b) by 897 days.

(21) Appl. No.: 12/317,936

(22) Filed: Dec. 30, 2008

(65) Prior Publication Data

US 2010/0168747 A1    Jul. 1, 2010

(51) Int. Cl.
*A61B 17/16* (2006.01)
*A61B 17/32* (2006.01)

(52) U.S. Cl. ............ 606/80; 606/79; 606/170; 606/180

(58) Field of Classification Search ............. 606/79–85, 606/167, 170, 180
See application file for complete search history.

(56) References Cited

U.S. PATENT DOCUMENTS

| | | | |
|---|---|---|---|
| 4,672,964 A | 6/1987 | Dee et al. |
| 4,788,976 A | 12/1988 | Dee |
| 4,842,578 A | 6/1989 | Johnson et al. |
| 5,322,505 A | 6/1994 | Krause et al. |
| 5,411,514 A | 5/1995 | Fucci et al. |
| 5,467,763 A | 11/1995 | McMahon et al. |
| 5,474,571 A | 12/1995 | Lang et al. |
| 5,510,070 A | 4/1996 | Krause et al. |
| 5,514,157 A | 5/1996 | Nicholas et al. |
| 5,540,706 A | 7/1996 | Aust et al. |
| 5,549,637 A | 8/1996 | Crainich |
| 5,601,583 A | 2/1997 | Donahue et al. |
| 5,620,447 A | 4/1997 | Smith et al. |
| 5,707,350 A | 1/1998 | Krause et al. |
| 5,743,456 A * | 4/1998 | Jones et al. ............... 227/176.1 |
| 5,833,692 A | 11/1998 | Cesarini et al. |
| 5,879,353 A | 3/1999 | Terry |
| 5,928,239 A | 7/1999 | Mirza |
| 5,993,463 A | 11/1999 | Truwit |
| 6,322,565 B1 | 11/2001 | Garner et al. |
| 6,418,935 B1 | 7/2002 | Yoon et al. |
| 6,607,561 B2 | 8/2003 | Brannon |

(Continued)

FOREIGN PATENT DOCUMENTS

WO    2006033888 A2    3/2006

*Primary Examiner* — Thomas Barrett
*Assistant Examiner* — Michael T Schaper
(74) *Attorney, Agent, or Firm* — Lerner, David, Littenberg, Krumholz & Mentlik, LLP

(57) ABSTRACT

A surgical instrument includes a deflectable cutting element extending from the distal end of the instrument. The deflection of the cutting element is controllable based on a user operating a moveable member of the instrument. The deflectable cutting element is normally disposed within a circumferential region defined by the distal end of the instrument. The moveable member can be moved in relation to the instrument to deflect the deflectable cutting element, such that the cutting element is at least partially outside of the circumferential region. The extent that the cutting element is outside of the circumferential region is a function of the position to which the moveable member is moved in relation to the instrument. The instrument further includes direct imaging of the distal end, such that the deflection of the cutting element for selective removal of bone tissue at the distal end of the instrument can be controlled in real-time.

7 Claims, 24 Drawing Sheets

U.S. PATENT DOCUMENTS

| | | |
|---|---|---|
| 6,827,720 B2 | 12/2004 | Leali |
| 6,863,668 B2 | 3/2005 | Gillespie et al. |
| 6,863,676 B2 * | 3/2005 | Lee et al. .................. 606/159 |
| 6,923,813 B2 | 8/2005 | Phillips et al. |
| 7,160,306 B2 | 1/2007 | Matsuzaki et al. |
| 7,445,595 B2 | 11/2008 | Brannon |
| 2003/0088245 A1 | 5/2003 | Woloszko et al. |
| 2004/0133208 A1 | 7/2004 | Weikel et al. |
| 2004/0230211 A1 * | 11/2004 | Moutafis et al. ............ 606/167 |
| 2005/0033292 A1 | 2/2005 | Teitelbaum et al. |
| 2005/0033293 A1 | 2/2005 | Yoon |
| 2005/0165420 A1 * | 7/2005 | Cha ............................. 606/150 |
| 2005/0261692 A1 * | 11/2005 | Carrison et al. ............... 606/79 |
| 2005/0277968 A1 * | 12/2005 | Lee ............................... 606/170 |
| 2006/0057184 A1 | 3/2006 | Nycz et al. |
| 2006/0063973 A1 | 3/2006 | Makower et al. |
| 2006/0095059 A1 | 5/2006 | Bleich et al. |
| 2006/0184187 A1 * | 8/2006 | Surti ............................. 606/170 |
| 2006/0229624 A1 * | 10/2006 | May et al. ...................... 606/79 |
| 2007/0179340 A1 | 8/2007 | Jorgensen |
| 2007/0213735 A1 | 9/2007 | Saadat et al. |
| 2007/0213833 A1 | 9/2007 | Mears et al. |
| 2007/0225740 A1 * | 9/2007 | Suddaby ....................... 606/170 |
| 2007/0239138 A1 | 10/2007 | Lawrence et al. |
| 2007/0249899 A1 | 10/2007 | Seifert |
| 2008/0045881 A1 | 2/2008 | Teitelbaum et al. |
| 2008/0051812 A1 | 2/2008 | Schmitz et al. |
| 2008/0097154 A1 | 4/2008 | Makower et al. |
| 2008/0097295 A1 | 4/2008 | Makower et al. |
| 2008/0114364 A1 * | 5/2008 | Goldin et al. ................. 606/79 |
| 2008/0161809 A1 * | 7/2008 | Schmitz et al. ............... 606/79 |
| 2008/0195128 A1 * | 8/2008 | Orbay et al. .................. 606/170 |

* cited by examiner

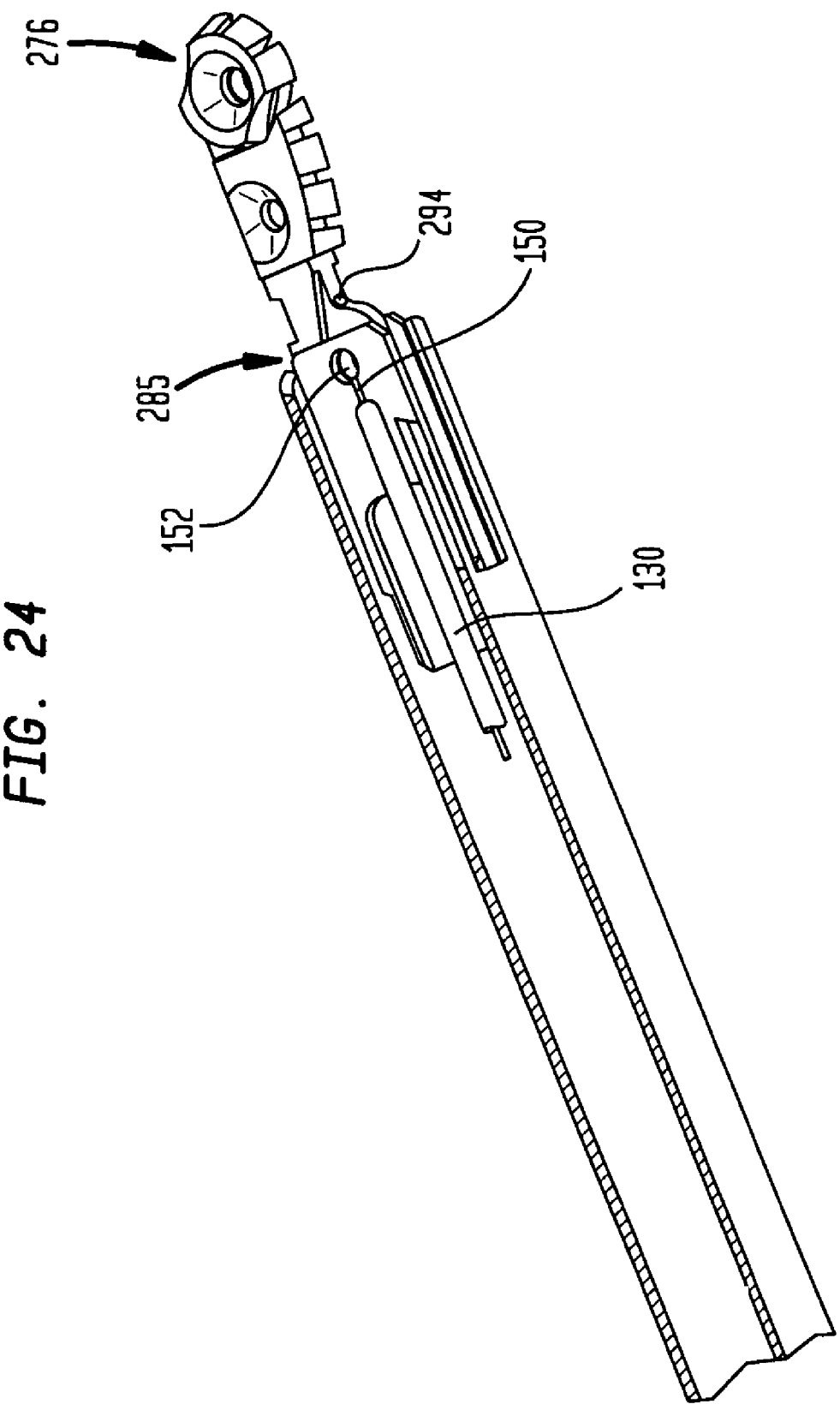

METHOD AND APPARATUS FOR REMOVAL OF TISSUE

FIELD OF THE INVENTION

The present invention relates to method and apparatus for tissue removal and, more particularly, a surgical instrument having a deflectable cutting element, and method for using same, for selectively removing tissue.

BACKGROUND OF THE INVENTION

The treatment of diseases of long bones often requires the removal of a portion or all of the diseased bone.

For example, removal of necrotic bone tissue is considered to be an important part of the treatment of osteonecrosis of the femoral head. Osteonecrosis of the femoral head is a disease caused by the occlusion of blood flow to or within the femoral head, which leads to the progressive necrosis of bone in the load bearing region. In osteonecrosis, as the bone dies, a lesion is formed below the subchondral bone. The lesion will grow until there is insufficient structural support of the subchondral bone and the femoral head collapses in the load bearing area. Early detection and intervention, particularly by removal of all of the necrotic bone, has been shown to retard and/or reverse the progression of the disease.

One method of treatment for osteonecrosis of the femoral head is core decompression. Core decompression, for example, can be performed by using a trephine or drill to remove a cylindrical core from within the femoral head. The trephine or drill is introduced into the femoral head through a lateral approach extending from the lateral cortex, typically distal to the greater trochanter, through the neck and into the necrotic region. Such core decompression procedure is performed under fluoroscopy to target necrotic regions. Necrotic bone may signal osteoclasts to initiate bone remodeling, but in osteonecrosis the remodeling mechanism is inhibited so necrotic bone may be removed without concurrent replacement. This will lead to collapse of the femoral head. The core decompression removes portions of the necrotic bone, thereby creating pathways to healthy bone structures and prompting the initiation of remodeling. The procedure only moderately targets the necrotic bone and does not remove all necrotic regions. The remaining necrotic regions may inhibit complete remodeling of the femoral head. The use of a trephine or drill to perform core decompression also has the risk of perforating the cartilage if the trephine or drill is inserted too deeply.

Core decompression also can include the use of a high speed burr and endoscope. For instance, after the cylindrical core is removed with the trephine or drill, a high speed spherical burr is introduced into the femoral head. This procedure is performed under fluoroscopy to avoid perforation, which increases the radiation exposure for the surgeon. Bone beyond the boundary of the cylindrical walls of the osseous tunnel is removed as the burr is moved around. To determine the amount of bone removed, the burr is removed and the endoscope is introduced into the head for visualization of the cavity. The alternation between the burr and endoscope is repeated many times, which significantly slows the procedure. In addition, since the cutting is not performed under real-time, direct visualization, the risk of penetrating the subchondral bone and perforating the articular cartilage as well as the removal of healthy bone is very high. In addition, the reach of the burr of the typical instrument used for bone decompression beyond the walls of the osseous tunnel is limited by the amount the shaft of the burr can be angled within the tunnel, thereby preventing the removal of all necrotic bone.

Further, a more invasive core decompression procedure involves exposing the femoral neck through an open anterior approach, and cutting an access window in the neck through which a series of small curettes and/or powered burr are introduced and the necrotic bone removed. In addition to being particularly invasive, such bone decompression technique is slow, and risks perforating the articular cartilage and removal of healthy bone.

Another therapeutic technique can include removal of a cylindrical core using a trephine or drill, and then implanting a vascular graft obtained from the fibula in the space that the core had occupied. The vascular graft is reattached to the circulatory system and provides structural support for the collapsed head as well as an osteoinductive scaffold to enable bone remodeling. Although this fibular grafting procedure has a relatively high success rate, which is attributable to the increase of blood flow in the femoral head, the duration of the surgical procedure is relatively lengthy, and may last up to four hours.

Therefore, there exists a need for method and apparatus for performing tissue removal, such as from the femoral head, precisely and with minimal invasiveness.

SUMMARY OF THE INVENTION

In accordance with one aspect of the present invention, a surgical instrument includes a deflectable cutting device, a coupling element coupling the cutting device with a moveable member, and a housing having an axis and defining a bore extending between a first end and a second end. The second end of the housing defines a circumferential region and is coupled to the cutting device, the moveable member is coupled to the housing, and the coupling element extends through the bore of the housing to the second end of the housing. A first flow path for conveying a fluid extends through the bore of the housing to the second end of the housing, and a second flow path for conveying a fluid extends between the first end and the second end of the housing and is distinct from the first flow path. The first flow path or the second flow path is for receiving an optical waveguide having a lens tip disposed adjacent the second end of the housing. In an at rest condition of the instrument, the cutting device is disposed within the circumferential region defined by the second end of the housing. The moveable member is operable for applying a force on the coupling element to cause the cutting device to be disposed at least partially outside the circumferential region defined by the second end of the housing, such that the instrument is in a deflected condition.

In accordance with another aspect of the present invention, a surgical instrument includes a tubular member having an axis, a first end coupled to a drive housing and a second end coupled to a cutting apparatus including a rotatable and deflectable cutting element, wherein the second end of the tubular member defines a circumferential region. The instrument further includes a drive shaft having a first end coupled to a rotatable drive member in the housing and a second end coupled to the cutting element, wherein the drive shaft translates rotational motion at the drive member to the cutting element to cause rotation of the cutting element. In addition, the instrument includes a thrust member having a first end within the housing and a second end coupled to a resilient member in the cutting apparatus, wherein the resilient member is coupled to the cutting element and bending of the resilient member causes movement of the cutting element away from the axis of the tubular member. A first fluid flow path extends from within the housing, through a bore defined in the tubular member, and terminates at the cutting apparatus. The bore of the tubular member includes a second fluid flow path extending between the drive housing and the cutting apparatus and which is distinct from the first flow path. The first flow path or the second flow path is for receiving an optical waveguide having a lens tip positionable proximate the cutting apparatus. In an at rest condition of the instrument, the cutting element is disposed within the circumferential region defined by the second end of the tubular member. A moveable member is coupled to the first end of the thrust member and operable to set the instrument to a deflected condition. When the instrument is in the deflected condition, the moveable member applies a force at the first end of the thrust member causing the second end of the thrust member to bend the resilient member, such that the cutting element is moved away from the axis of the tubular member and is disposed at least partially outside the circumferential region defined by the second end of the tubular member.

In accordance with another aspect of the present invention, a surgical instrument includes a tubular member having an axis, a first end coupled to a housing and a second end coupled to a cutting apparatus including a deflectable cutting element, wherein the second end of the tubular member defines a circumferential region. A first fluid flow path extends from within the housing, through a bore defined by the tubular member, and terminates at the cutting apparatus. The bore of the tubular member includes a second fluid flow path extending between the drive housing and the cutting apparatus and which is distinct from the first flow path. The first flow path or the second flow path is for receiving an optical waveguide having a lens tip positionable proximate the cutting apparatus. A cable extends through a bore defined in the cutting apparatus, wherein the bore extends transverse to the axis of the tubular member. The cable has first and second ends fixedly coupled to first and second moveable cable fixing elements, respectively, contained in the housing. In an at rest condition of the instrument, the cutting element is disposed within the circumferential region defined by the second end of the tubular member. A moveable member is coupled to the first fixing element and operable to set the instrument to a deflected condition. When the instrument is in the deflected condition, the moveable member applies a force to the first fixing element to cause the first end of the cable to move away from the cutting element for causing the cutting element to rotate away from the axis of the tubular member, such that the cutting element is disposed at least partially outside the circumferential region defined by the second end of the tubular member.

In accordance with a further aspect of the present invention, a method for removing tissue includes inserting a distal end of a tubular element of a surgical instrument into an osseous tunnel with the instrument in an at rest condition, wherein the tubular element has an axis, wherein the distal end of the tubular element defines a circumferential region and is coupled to a deflectable cutting device, wherein the tunnel defines a circumferential region substantially corresponding to the circumferential region defined by the distal end of the tubular element and, wherein in the at rest condition of the instrument the cutting device is disposed within the circumferential region defined by the distal end of the tubular element. The method further includes supplying fluid to the distal end of the tubular element through a first flow path extending through a bore defined in the tubular element; receiving, at the proximal end of the tubular element, the fluid supplied to the distal end of the tubular element from a second fluid flow path in the bore of the tubular element extending between a proximal end and the distal end of the tubular element, wherein the second flow path is distinct from the first flow path and wherein an optical waveguide extends through the first flow path or the second flow path to the distal end of the tubular element; controllably operating the instrument to move the cutting device away from or towards the axis of the tubular element and be disposed at least partially outside of the circumferential region, such that the instrument is in a deflected condition; and causing the cutting device to cut selected regions of tissue at the distal end of the tunnel when the instrument is in the deflected condition, based on images of the distal end of the tunnel supplied by the waveguide.

BRIEF DESCRIPTION OF THE DRAWINGS

Other objects and advantages of the present invention will be apparent from the following detailed description of the present preferred embodiments, which description should be considered in conjunction with the accompanying drawings in which like reference indicate similar elements and in which:

FIG. 24 is a perspective view of a portion of the instrument of FIG. 12 in the at rest condition.

DETAILED DESCRIPTION

Figure 1:
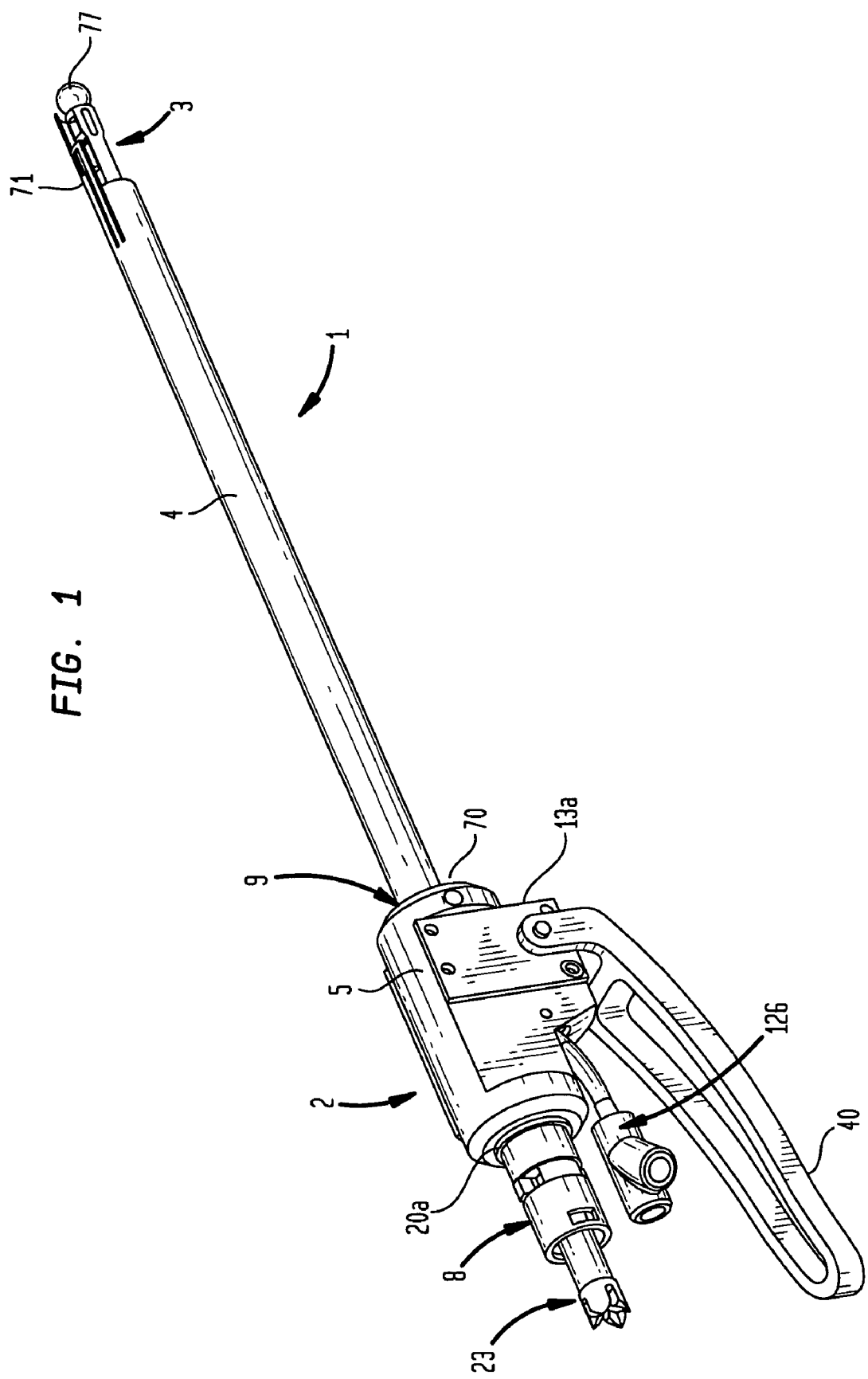
FIG. 1 is a perspective view of an exemplary surgical instrument, in accordance with an aspect of the present invention, in an at rest condition.

FIG. 1 is an exemplary surgical instrument 1 for removal of tissue, such as necrotic bone tissue from the femoral head of a hip joint, in accordance with an aspect of the present invention. The instrument 1 is operable for precise and selective removal of bone tissue within and outside a circumferential region defined by the distal end of the instrument 1. Referring to FIG. 1, the instrument 1 includes a power drive portion 2 on a first end 70 of a main tube 4 and an articulating cutting burr portion 3 on a second end 71 of the main tube 4.

Figure 2:
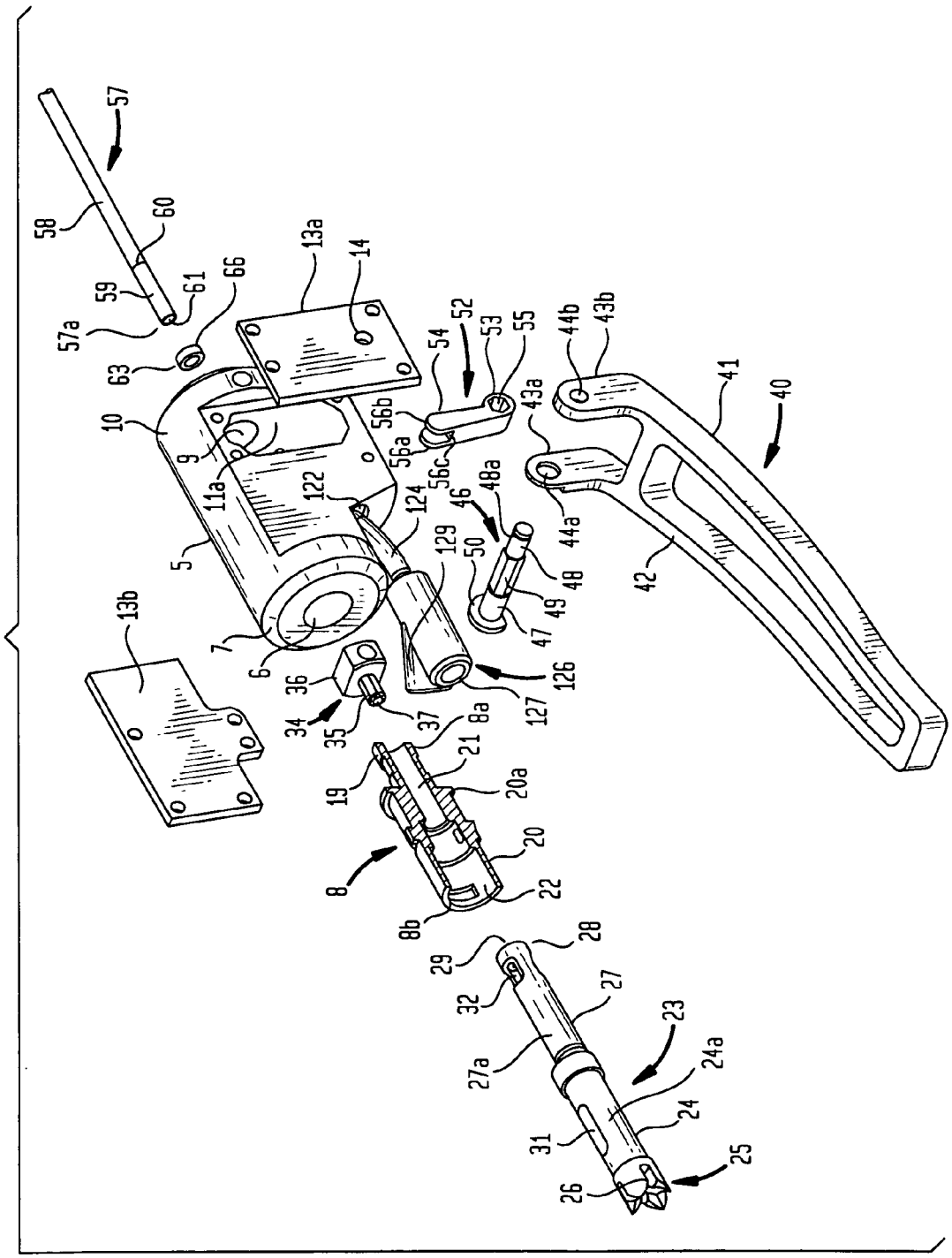
FIG. 2 is an exploded view of an exemplary drive portion of the surgical instrument of FIG. 1.
Figure 3:
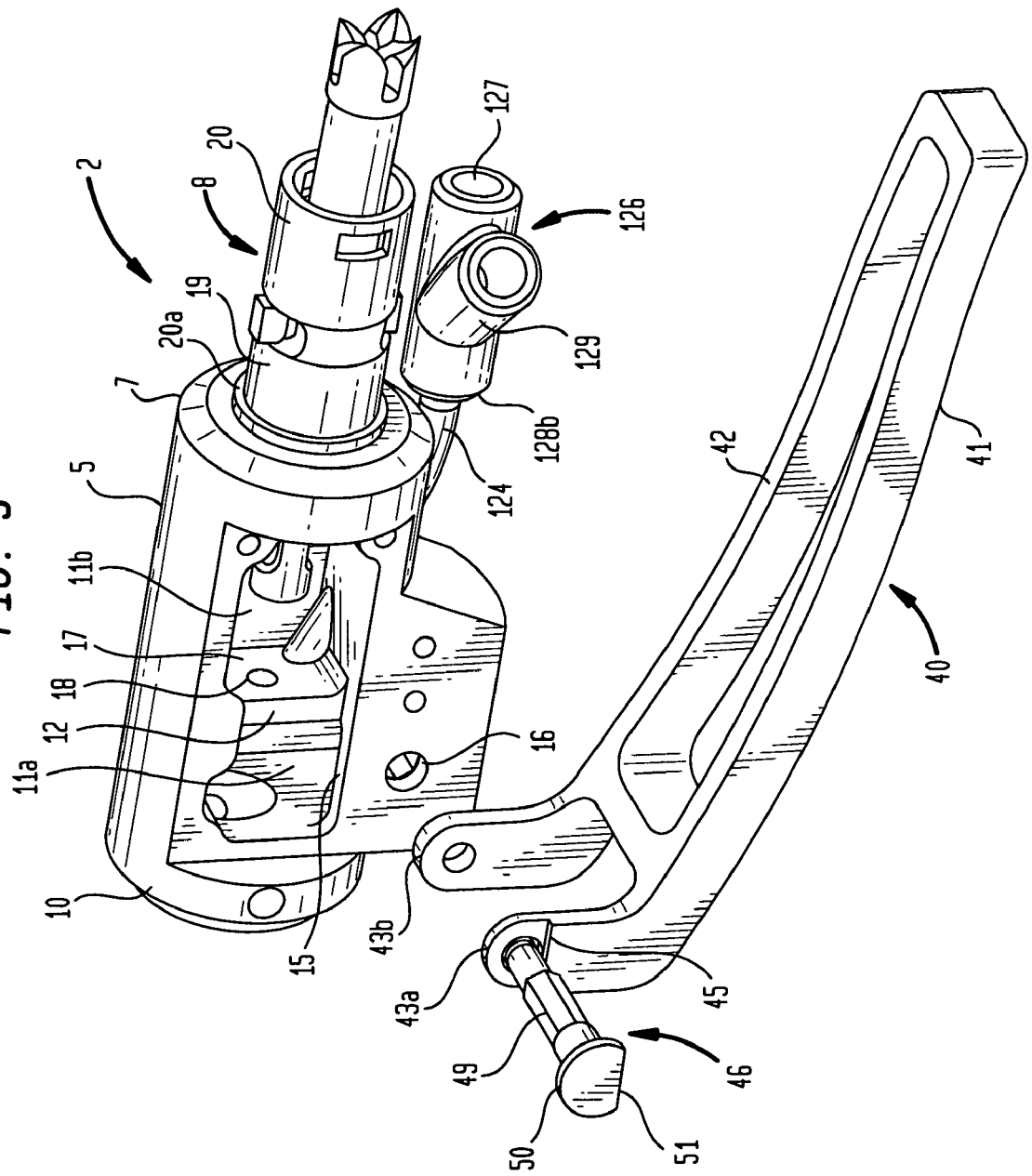
FIG. 3 is an exploded view of a portion of the drive portion of FIG. 2.
Figure 4:
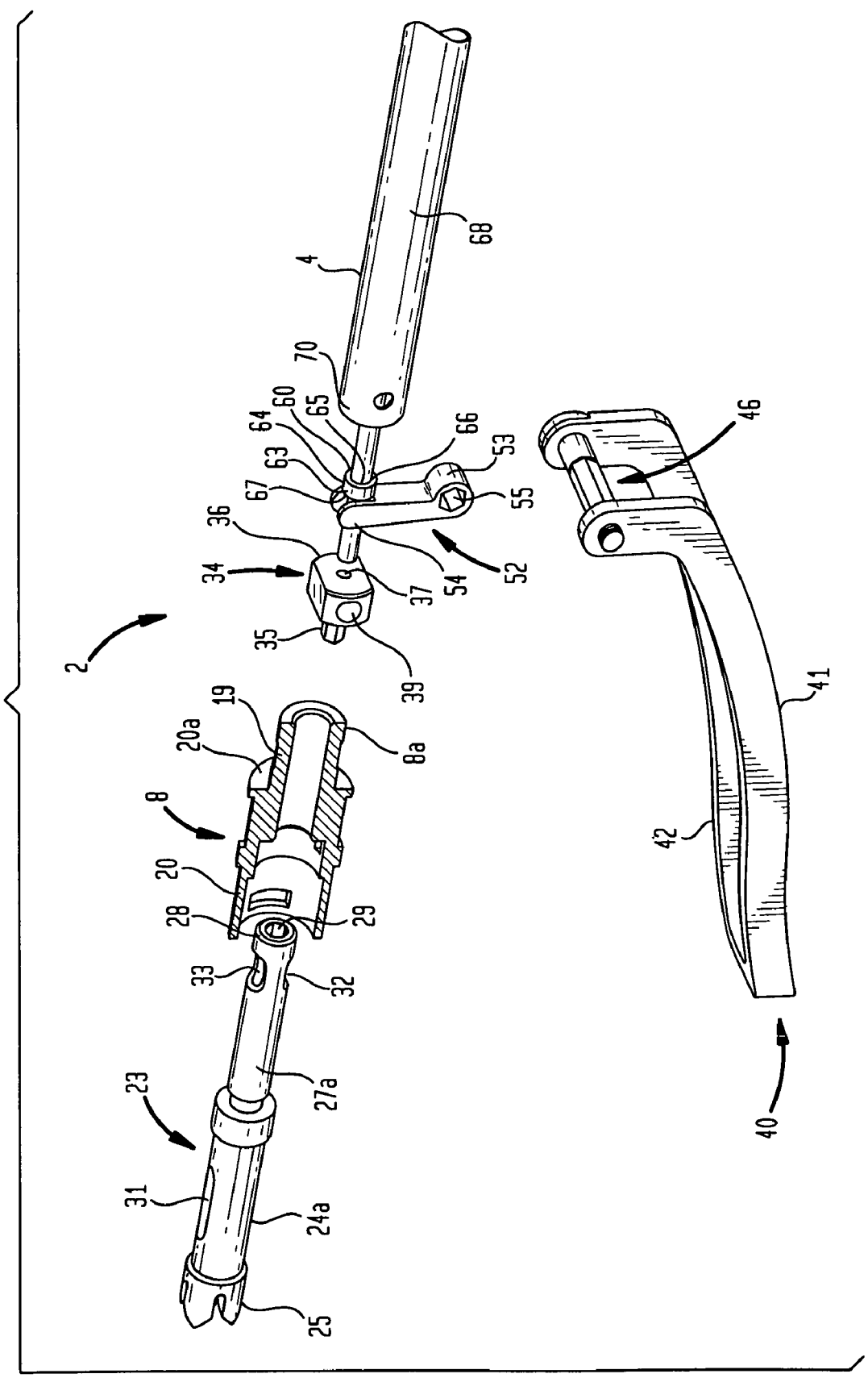
FIG. 4 is an exploded view of another portion of the drive portion of the instrument of FIG. 1.
Figure 5:
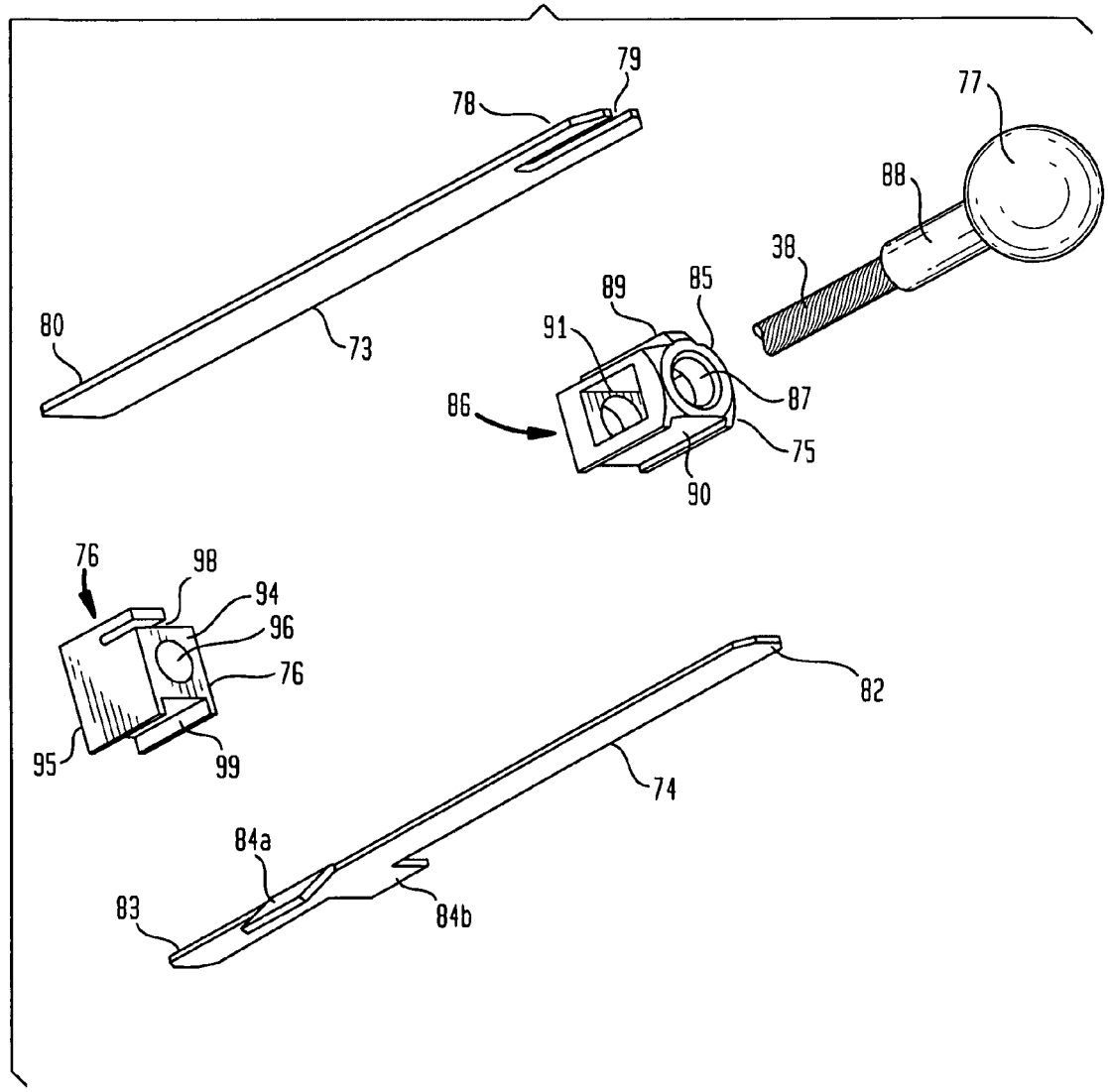
FIG. 5 is an exploded view of an exemplary burr portion of the instrument of FIG. 1.

Further referring to FIGS. 2, 3 and 4, the power drive portion 2 includes a main housing 5, a driver coupling connector 8, a drive fitting 23, a flexible shaft fitting 34, a lever 40, a hinge pin 46, a thrust fork 52, a thrust collar 63 and a thrust tube 57. The housing 5 includes a first bore 6 on a first end 7 for coupling with the driver connector 8, and a second bore 9 on a second end 10 opposite the first end 7 for coupling with the main tube 4. The main housing 5 further includes a first recessed pocket 11a in proximity to the second end 10, and a second recessed pocket 11b in proximity with the first end 7. The first and second recessed pockets 11a and 11b are spaced apart from each other, and defined in part, by a first wall portion 17 disposed between the pockets 11a and 11b. The first wall portion 17 further defines a through bore 18, and a third recessed pocket 12. The bores 6, 9 and 18 are axially aligned. The pocket 12 connects the first recessed pocket 11a with the second recessed pocket 11b within the housing 5. The first recessed pocket 11a further includes a second wall portion 15 defining a through bore 16. The bore 16 extends in a direction perpendicular to the axis along which the bore 9 extends.

The housing 5 also includes first and second plates 13a and 13b, such as formed from plexiglass or another liquid impermeable material, that cover the first and second recessed pockets 11a and 11b to form two water tight compartments interconnected by the recessed pocket 12. The first plate 13a contains a through bore 14 extending perpendicular to its thickness and the axis along which the bore 9 extends.

Figure 7:
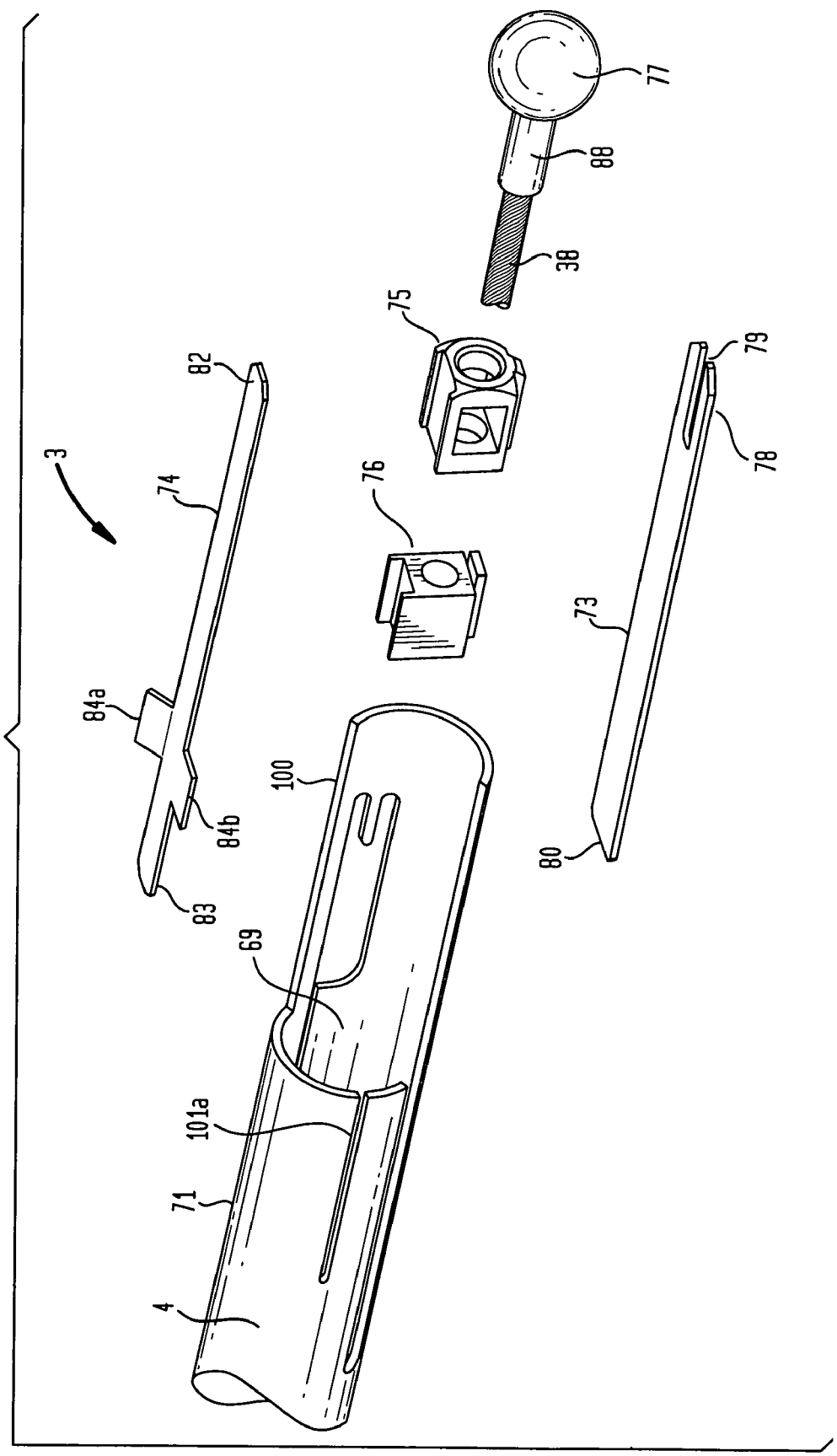
FIG. 7 is another exploded view of the burr portion of the instrument of FIG. 1.
Figure 8:
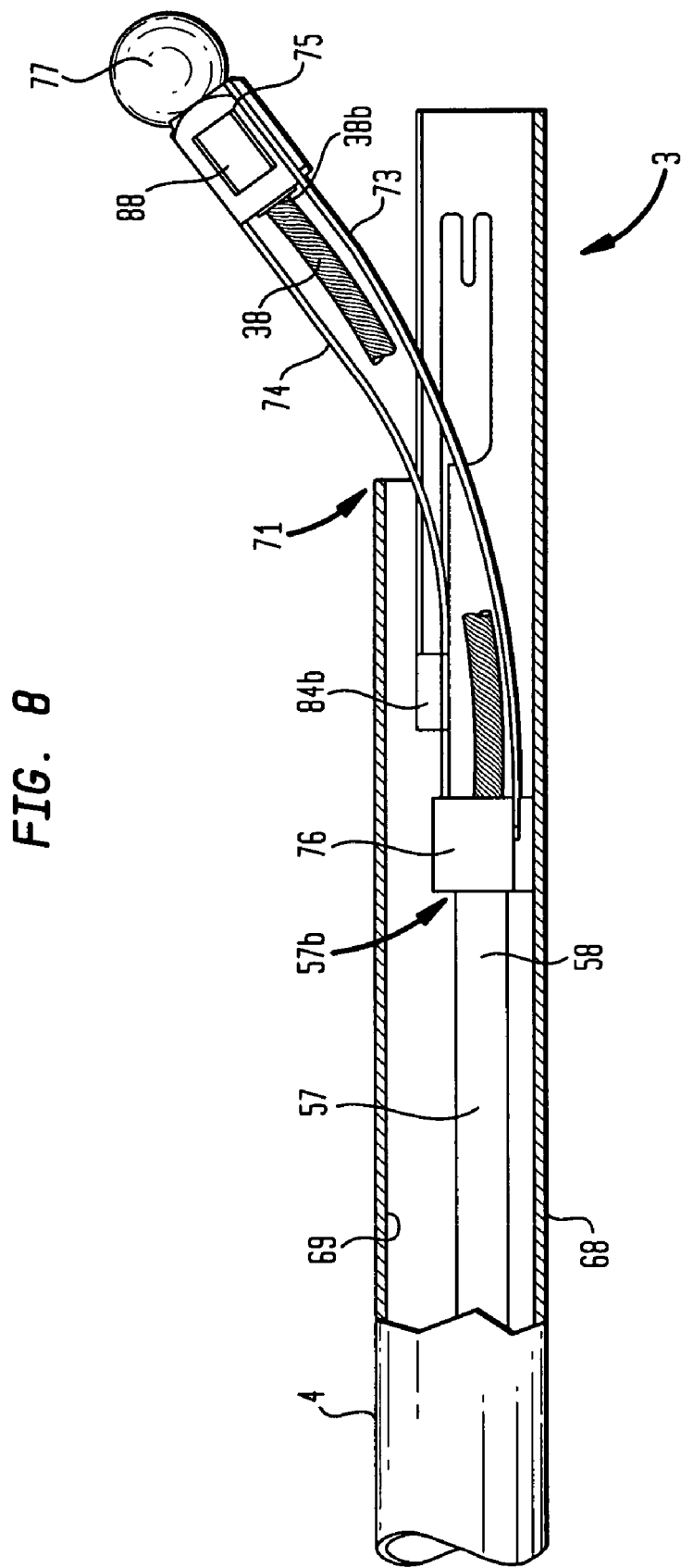
FIG. 8 is a cross-sectional view of the burr portion of the instrument of FIG. 1 in a deflected condition.

Referring to FIGS. 1, 4 and 8, the main tube 4 has an outside surface 68 and an inside surface 69. The first end 70 of the tube 4 is for coupling with the main housing 5, and the second end 71 of the tube is for coupling with the articulating cutting burr portion 3, as discussed in detail below in the text accompanying the description of FIGS. 5-8.

Referring to FIGS. 1-4, the drive connector 8 includes a first cylindrical portion 19 on a first end portion 8a for coupling with the bore 6 of the main housing 5, and a second cylindrical portion 20 on a second end portion 8b for quick-connection coupling with a conventional power drive head unit (not shown), such as a Formula power shaver sold by Stryker Corporation. The first cylindrical portion 19 and the second cylindrical portion 20 are axially aligned. In addition, the first cylindrical portion 19 has a smaller outer diameter than the outer diameter of the second cylindrical portion 20, such that a shoulder 20a is formed between the former and latter. The driver connector 8 further includes a through bore 21 which is coaxial with the first and second cylindrical portions 19, 20. In addition, the driver connector 8 includes a counterbore 22 extending from the end portion 8b and which is coaxial with the second cylindrical portion 20. The axial length or depth of the counterbore 22 is shorter than the axial length of the second cylindrical portion 20.

The drive fitting 23 contains a first cylindrical portion 24 terminating at a first end 25. The first end 25 includes splines 26 for engagement with, and enabling the transmission of torque from, the drive head of a power drive unit (not shown). The drive fitting 23 further includes a second cylindrical portion 27, which is coaxial with the first cylindrical portion 24 and terminates in a second end 28 opposite the first end 25. The second end 28 includes a hex or splined hole 29 coaxial with the first and second cylindrical portions 24 and 27 and for coupling with the flexible shaft fitting 34, as discussed below.

Referring to FIGS. 2 and 4, the first cylindrical portion 24 of the fitting 23 includes a wall 24a, and a first aperture 31 is defined in the wall 24a in proximity to the first end 25. The second cylindrical portion 27 includes a wall 27a, and a second aperture 32 is defined in the wall 27a in proximity with the second end 28. The apertures 31 and 32 extend through the first and second cylindrical portions 24 and 27, respectively, in a direction generally perpendicular to the axis of the cylindrical portions 24 and 27. A bore 33 extends from the second end 28 of the second cylindrical portion 27 to a depth intersecting the first aperture 31 and the second aperture 32, and the bore 33 is centered about the axis along which the cylindrical portions 24 and 27 extend. The second cylindrical portion 27 is sized to be received through, and act as a bearing coupling with, the through bore 21 of the driver connector 8.

Referring to FIGS. 2, 4, 10 and 11, the flexible shaft fitting 34 includes a male hex or spline fitting 35 and an adjacent cylindrical portion 36. The cylindrical portion 36 is coaxial with the hex or spline fitting 35 and a through bore 37 which extends through the entire length of the fitting 34. The bore 37 is sized to receive an end 38a (not shown) of a braided flexible drive shaft 38. The male hex or spline fitting 35 is sized and configured to slideably couple with the hex or splined hole 29 of the drive fitting 23. The cylindrical portion 36 defines a threaded hole 39 extending in a direction generally perpendicular to the axis of the cylindrical portion 36 and having a depth intersecting the through bore 37.

When the instrument 1 is assembled, a set screw (not shown) is threaded into the threaded hole 39 and secures the end 38a of the braided flexible drive shaft 38 to the fitting 34. In addition, the splined hole 29 of the drive fitting 23 is coupled to the spline fitting 35 of the shaft fitting 34, such that the fitting 23 can transmit torque to the fitting 34 for causing rotation of the fitting 34, based on a power unit (not shown) being coupled to and causing rotation of the fitting 23. The rotating fitting 34, in turn, causes rotation of the shaft 38 in the same direction as the fitting 23.

Referring to FIGS. 1-4 and 10-11, the lever 40 includes a far side surface 41 for contact with a user's hand, and a near side surface 42 opposite the far side surface 41. The near surface 42 contains first and second projecting tabs 43a, 43b. The first and second projecting tabs 43a, 43b are spaced from and are substantially parallel to each other, and extend in a direction opposite to the far side surface 41. The first and second projecting tabs 43a, 43b include coaxial through bores 44a and 44b, respectively, which extend perpendicular to the first and second tabs 43a, 43b. The first projecting tab 43a contains a recessed cut 45 oriented perpendicularly to the axis of the first and second bores 44a and 44b.

Referring to FIGS. 2-4, the hinge pin 46, which connects the lever 40 to the main housing 5, has a first cylindrical portion 47 on a first end and a second cylindrical portion 48 on a second end opposite the first end. The hinge pin 46 includes a hex or spline portion 49 disposed between the first and second cylindrical portions 47, 48. The first and second cylindrical portions 47, 48 and the hex or spline portion 49 are coaxially aligned. The hinge pin 46 further includes an abutting shoulder 50 on the first end which is oriented coaxially with and disposed adjacent to the first cylindrical portion 47. The shoulder 50 contains a flat surface 51 oriented parallel to the axis of the first cylindrical portion 47, and configured and sized to correspond to the configuration and size of the recessed cut 45.

The thrust fork 52 has a first end 53 and a second end 54 opposite the first end 53. The first end 53 has a through hex or splined bore 55 sized for mating with the hex or spline portion 49 of the hinge pin 46, and when mated to the spline portion 49 forms a non-rotating junction, as discussed below. The second end 54 of the thrust fork 52 includes substantially parallel first and second tabs 56a, 56b, which project in a direction away from the first end 53 and are spaced apart from each other to form a slot 56c. The first and second tabs 56a, 56b are oriented such that the median plane of the slot 56c is perpendicularly oriented with respect to the axis of the through hex or splined bore 55 of the thrust fork 52.

Referring to FIGS. 1-4 and 10-11, when the instrument 1 is assembled, the first cylindrical portion 47 of the hinge pin 46 extends through the bore 44a of the first tab 43a of the lever 40 and the bore 16 of the main housing 5. Also, the second cylindrical portion 48 of the hinge pin 46 extends through the bore 44b of the second tab 43b of the lever 40 and the bore 14 of the first side plate 13a. The flat surface 51 on the abutting shoulder 50 of the hinge pin 46 couples with the recessed cut 45 of the first projecting tab 43a of the lever 40 to prevent rotation of the hinge pin 46 with respect to the lever 40. Thus, the pin 46 forms a rotatable hinged connection between the lever 40 and the main body 5. In addition, the hex or spline portion 49 of the hinge pin 46 is mated with the splined bore 55, such that the hinge pin 46 does not rotate with respect to the bore 55. End 48a of the hinge pin 46, which is opposite the first end, includes threading to which a nut (not shown) is threaded to prevent the pin 46 from becoming uncoupled from the main body 5 by sliding out of the hole 16, but still permit the lever 40 to rotate toward and away from the housing 5. Alternatively, a groove and "C" snap ring can be used in place of the combination of the nut and threading on the pin for maintaining the pin 46 coupled to the main body.

Referring to FIGS. 2, 4, 8, 10 and 11, the thrust tube 57 extends from within the main housing 5, through the tube 4 and to the burr portion 3. The tube 57 has a first cylindrical portion 58 and a second cylindrical portion 59, which extends from and is coaxial with the portion 58. The outside diameter of the portion 58 exceeds the outside diameter of the portion 59, such that a shoulder 60 is formed at the junction of the portions 58, 59. The tube 57 has an inside surface 61 having a constant diameter extending its entire length.

The thrust collar 63 has an outside surface 64, an inside surface 65, a first face 66 and a second face 67 opposite the first face 66. The first face 66 is sized for coupling against the shoulder 60 of the thrust tube 57, and the second face 67 is sized for coupling with the first and second tabs 56a and 56b of the thrust fork 52. The inside surface 65 of the thrust collar 63 has a diameter sized for coupling with the outside surface of the portion 59 of the thrust tube 57. The outside diameter of the surface 64 of the thrust collar 63 is larger than the width of the slot 56c formed between the first tab 56a and the second tab 56b of the thrust fork 52.

When the instrument 1 is assembled, the second portion 59 of the thrust tube 57 extends from adjacent the shaft fitting 34 in the recess 11b, through the bore 18 in the wall portion 17 and into the recess 11a. Within the recess 11a, the second portion 59 extends from the wall portion 17, through the slot 56c of the thrust fork 52, such that the tabs 56a and 56b of the thrust fork 52 are coupled to the second portion 59, and then through the thrust collar 63. The thrust collar 63 abuts against the tabs 56a and 56b and the shoulder 60 of the thrust tube 57. The portion 58 of the thrust tube 57 extends from within the recess 11a, through the bore 9 and then the tube 4, and terminates at the end 57b adjacent the end 71 of the tube 4.

FIGS. 5, 6, 7 and 8 show an exemplary embodiment of the articulating cutting burr portion 3 for coupling to the end 71 of the tube 4 of the instrument 1. The burr portion 3 includes a first leaf spring 73, a second leaf spring 74, a burr bearing housing 75, a tube cap 76 and a spherical burr 77. As described below, the burr portion 3 is for receiving and coupling to the end 38b of the braided flexible shaft 38, where the shaft 38 extends from the end 38a secured to the shaft fitting 34 within the housing 5, through the thrust tube 57 and out the end 71 of the tube 4. The first leaf spring 73 includes a first end 78 defining a slot 79 for coupling with the burr bearing housing 75, and a second end 80 opposite the first end 78 for coupling with the tube cap 76. The second leaf spring 74 includes a first end 82 for coupling with the burr bearing housing 75, and a second end 83 opposite the first end 82 for coupling with the tube cap 76. The second leaf spring 74 also includes two projecting tabs 84a and 84b located between the first end 82 and the second end 83.

The burr bearing housing 75 is generally rectangular in shape, and includes a first end 85, a second end 86 opposite the first end 85 and a through bore 87 extending from the first end 85 to the second end 86. The bore 87 is sized for receiving a shaft portion 88 of the spherical burr 77 therethrough. The burr bearing housing 75 further includes a rib 89 extending from the first end 85 to the second end 86 and sized for being received in the slot 79 of the first leaf spring 73. The burr bearing housing 75 also includes a recessed channel 90, located opposite of the rib 89 and extending from the first end 85 to the second end 86. The channel 90 is sized for receiving the first end 82 of the second leaf spring 74. In addition, the burr bearing housing 75 includes a through cutout window 91, located between the first end 85 and the second end 86 and oriented perpendicular to the rib 89 and the recessed channel 90. The first ends 78 and 82 of the leaf springs 73 and 74, respectively, are welded to the burr bearing housing 75 to form a permanent assembly. The shaft portion 88 has an inside surface 92 defining an interior diameter sized for receiving the end 38b of the braided flexible shaft 38. The shaft portion 88 of the spherical burr 77 is crimped or swaged to the end 38b of the braided flexible shaft 38 to form a permanent assembly.

The thrust tube cap 76 is generally rectangular in shape and includes a first end 94 and a second end 95 opposite the first end 94. The cap 76 also includes a through bore 96 extending from the first end 94 to the second end 95 and sized for receiving the braided flexible shaft 38 therethrough. In addition, the thrust tube cap 76 includes a counter bore 97 defined in the end 95 and which is for receiving the second end 57b of the thrust tube 57. The bore 97 is coaxial with, and has an inner diameter larger than that of, the through bore 96. The junction of the bores 96 and 97 forms a shoulder 97a, which the end 57b of the thrust tube 57 abuts against when the end 57b end of the thrust tube 57 is received in the bore 97 for the assembled instrument 1. Further, the thrust tube cap 76 includes a slot 98 for receiving the second end 80 of the first leaf spring 73. The slot 98 is oriented parallel to the axis of the through bore 96 and projects from the first end 94 towards, but does not extend to, the second end 95. The thrust tube cap 76 also includes a recessed channel 99 located opposite of the slot 98. The channel 99 extends from the first end 94 to the second end 95 of the thrust tube cap 76 and is sized for slideably receiving the second end 83 of the second leaf spring 74. The second end 80 of the first leaf spring 73 is welded to the thrust tube cap 76 at the slot 98 to form a permanent assembly.

Figure 6:
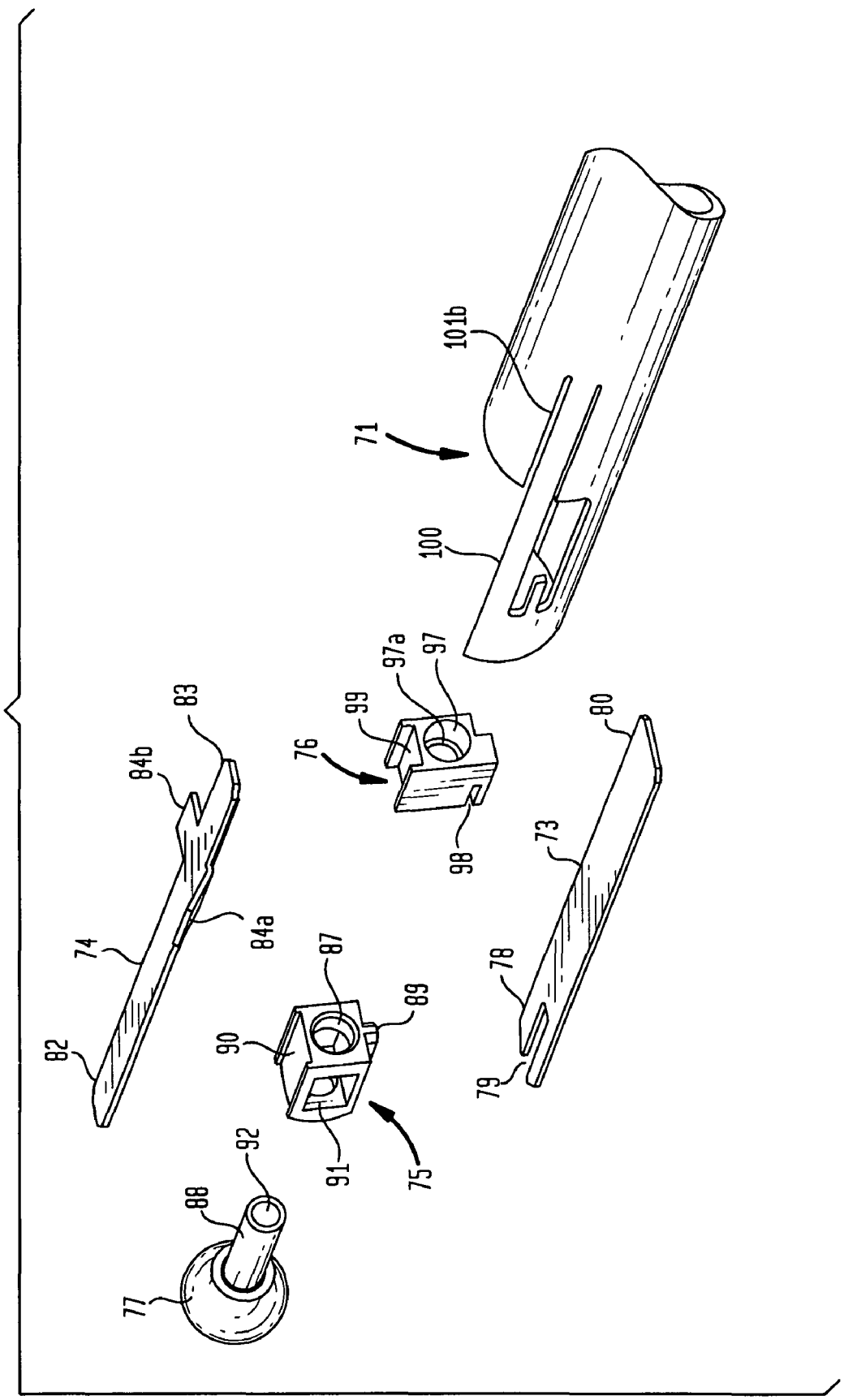
FIG. 6 is another exploded view of the burr portion of the instrument of FIG. 1.

Referring to FIGS. 6-8, the second end 71 of the main tube 4 includes a cutout 100 for receiving the articulating burr portion 3, and transverse slots 101a and 101b for receiving the projecting tabs 84b and 84a, respectively, of the second leaf spring 74. The first and second tabs 84a and 84b are welded to the slots 101a and 101b, respectively, to form a permanent assembly.

Figure 9:
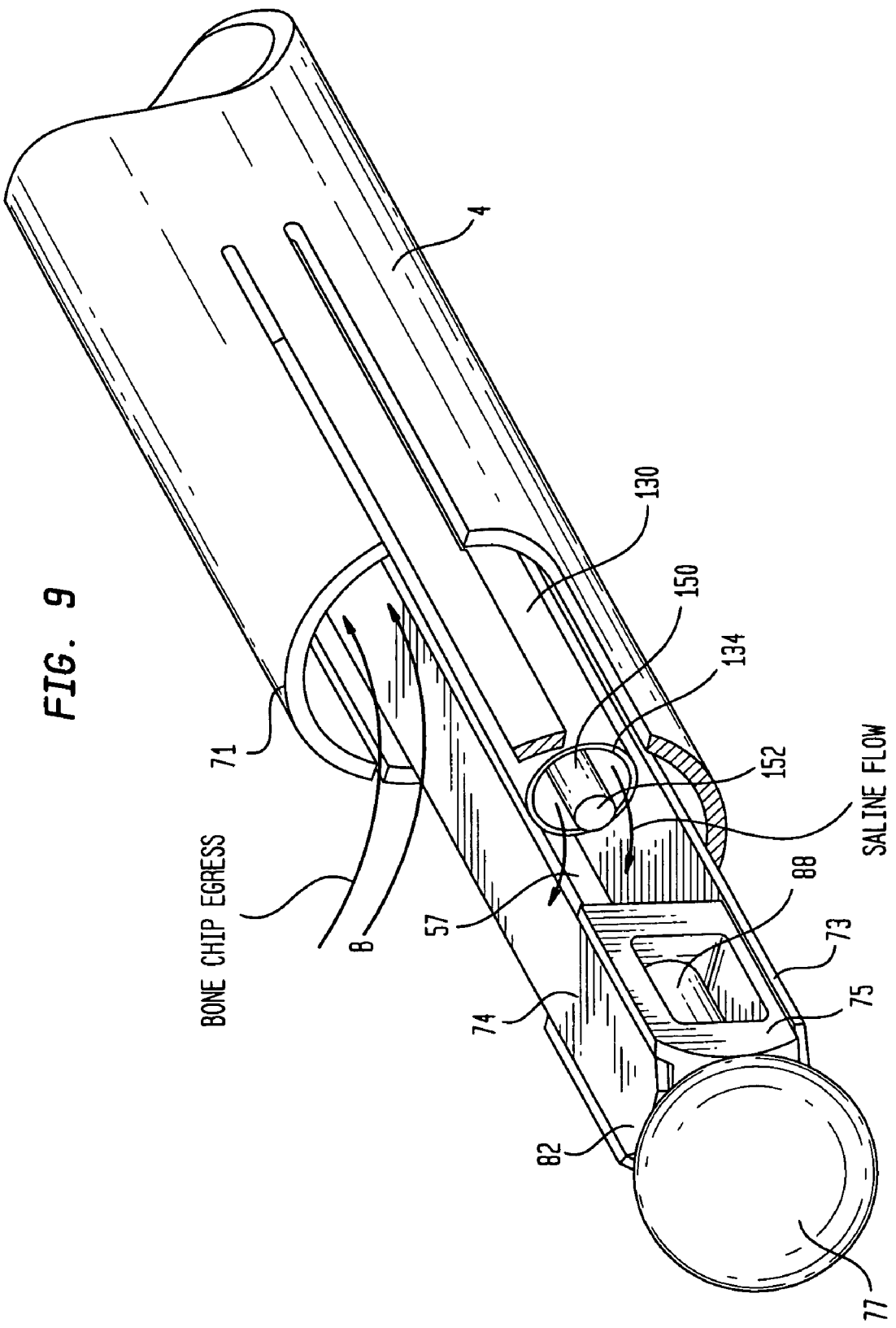
FIG. 9 is a perspective view of the burr portion of the instrument of FIG. 1 in an at rest condition.
Figure 10:
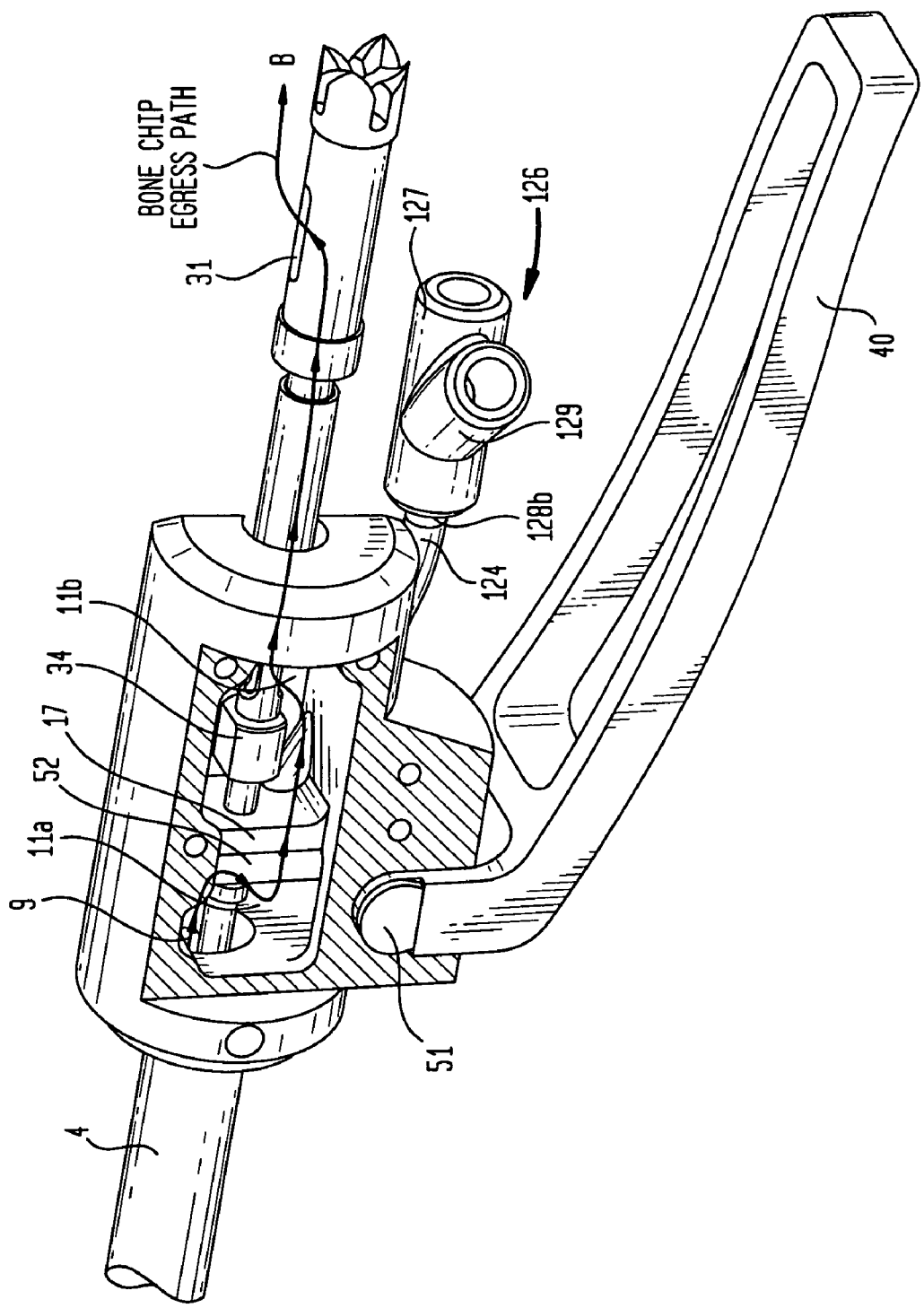
FIG. 10 is a perspective view of the drive portion of the instrument of FIG. 1.
Figure 11:
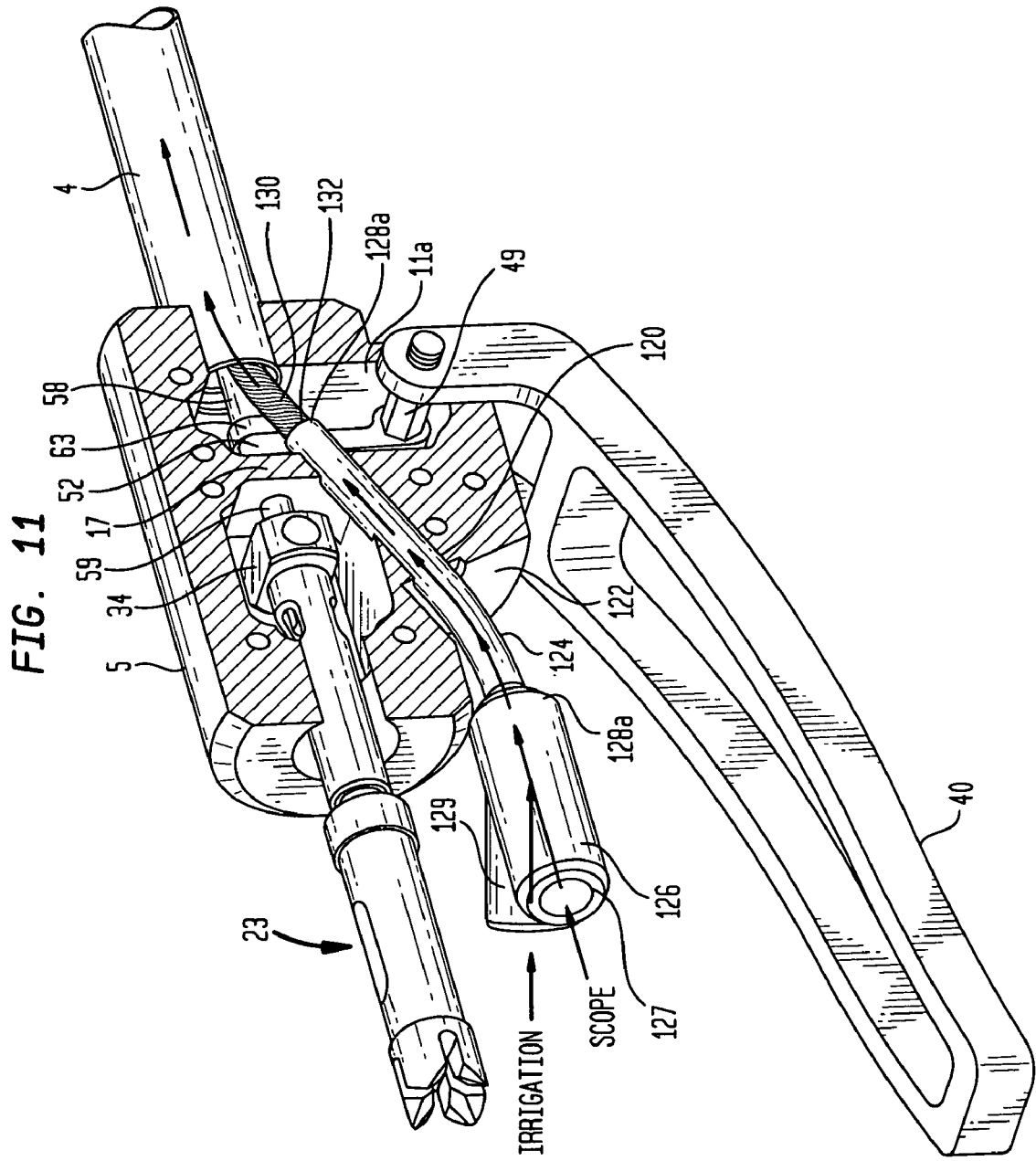
FIG. 11 is another perspective view of the drive portion of the instrument of FIG. 1.

Referring again to FIGS. 2 and 3, and also to FIGS. 9, 10 and 11, the main housing 5 includes a bore 120 extending from a proximal surface 122, through the housing 5 and opening into the recess 11a. A stem 124 of a Y fitting 126 extends through the bore 120, from the proximal surface 122 and to an end 128a that terminates in the recess 11a. The fitting 126 includes legs 127 and 129 which meet at an end 128b of the stem 124, which is opposite the end 128a. A flexible tube 130 at an end 132 is connected to the end 128a of the stem 124 to form a watertight seal. The tube 130 extends through the tube 4 and terminates at an end 134 adjacent the end 71 of the tube 4. The tube 130 has a sufficiently large inner diameter for receiving therethrough a fiber optic waveguide 150. Further, the tube 4 is sized to receive therethrough the tube 130 and the thrust tube 57 and to have unoccupied space extending along its length.

When the instrument 1 is assembled, the flexible shaft 38 interconnects the burr 77 with the shaft fitting 34, such that the burr 77 abuts the burr head housing 75 and the springs 73 and 74, the cap 76 abuts the end 57b of the tube 57, and the end 57a of the tube 57 abuts the cylindrical portion 36 of the shaft fitting 34. In addition, the outer diameter of the main tube 4, which in the exemplary embodiment is substantially cylindrical, at the second end 71 defines a circumferential region.

When the assembled instrument 1 is in an at rest condition, the leaf springs 73 and 74 are flat and parallel to each other, and the cap 76 is spaced from and does not contact the tabs 84b, 84a. When the leaf spring 73, 74 are flat, the shaft portion 88 is coaxial with the axis of the tube 4 and the entirety of the burr 77 is within the circumferential region defined at the second end 71 of the tube 4. Therefore, in the at rest condition of the instrument 1, no portion of the burr 77 is disposed a radial distance away from the axis of the tube 4 that exceeds the radius of the outer diameter of the tube 4 at the distal end 71.

When the assembled instrument 1 is in a deflected condition, the burr 77 has been caused to deflect or move away from the axis of the tube 4. To achieve a deflected condition of the instrument 1 when the instrument 1 is initially in the at rest condition, a user, such as a surgeon, initially applies a force to the surface 41 of the lever 40 in the direction of the housing 5, or depresses the lever 40. When the lever 40 is initially depressed, the lever 40 begins to rotate towards the housing 50, which causes the spline 49 of the pin 46 to engage with the spline 55 of the thrust fork 52. After the thrust fork 52 is so engaged by the pin 46, further depression of the lever 40 causes the tabs 56a, 56b of the thrust fork 52 to be forced against the collar 63 and, hence, apply an axial force in the direction of the burr portion 3 to the cylindrical portion 58 of the tube 57. The axial force on the portion 58, in turn, is translated to the cap 76, which then causes the cap 76 to begin to move axially away from the housing 5 and toward the projections 84a and 84b. When the cap 76 begins to move away from the housing 5, the first leaf spring 73 acts as a tensile member, and the first and second leaf springs 73, 74 begin to bend in unison and extend away from the axis of the tube 4, thereby causing a deflection of the burr 77 away from the axis of the tube 4 and beyond the circumferential region defined by the tube 4. As the springs 73, 74 are bent, energy is stored in the springs in correspondence to the extent the springs 73, 74 are bent away from the axis of the tube 4. The leaf springs 73, 74 have an exceptionally high torsional stiffness to provide that a lateral force applied on the burr 77, such as would ordinarily be experienced during cutting of tissue with the burr 77, would not impact the effectiveness of the cutting with the burr 77 when the instrument 1 is in the deflected condition. As the lever 40 is depressed further, the cap 76 moves further toward, and eventually contacts, the tabs 84a, 84b. When the cap 76 is in contact with the tabs 84a, 84b, the burr 77 is deflected to a maximum extent away from the axis of the tube 4. When the lever 40 is no longer depressed, or the extent that a user is depressing the lever 40 is decreased, the energy stored in the deflected springs 73, 74, which energy was created by the bending of springs 73, 74, causes the springs 73, 74 to straighten or be bent to a lesser extent, such that the cap 76 moves away from the tabs 84a, 84b and the thrust tube 57 moves in the direction of the housing portion 2.

In one embodiment, the instrument 1 may be used to perform a surgical procedure, such as to remove necrotic tissue from the femoral bone of a hip as part of core decompression procedure, as follows. Initially a small, lateral transcutaneous incision is made lateral to the femur and inferior to the greater trochanter of a hip. Then, a trephine or drill closely matching the outside diameter of the tube 4 at the end 71 is advanced through the femoral neck towards the approximate center of the femoral neck to define a tunnel having a diameter slightly larger than the outside diameter of the tube 4 at the end 71.

Referring to FIGS. 9 and 11, the instrument 1 is then prepared for use by inserting a flexible endoscope, such as the waveguide 150, through the leg 127 of the fitting 126. The waveguide 150 may be any optical energy signal conveying medium, as well known in the art, which can be coupled to a conventional direct vision apparatus (not shown) to provide for real-time and direct visualization of the region at lens tip 152 of the waveguide 150. The waveguide 150 is advanced through the fitting 126 and the tube 130 until the tip 152 of the waveguide 150 is positioned adjacent the burr bearing housing 75, as shown in FIG. 9.

After the waveguide 150 has been positioned in the tube 130, the instrument 1 is introduced into the osseous tunnel by first inserting the burr 77, followed by the tube 4, into the tunnel. When the instrument 1 is introduced into the tunnel, the instrument 1 is in the at rest condition, where the lever 40 is not depressed, such that the leaf springs 73 and 74 are flat and parallel to each other and the burr 77 is completely within the circumferential region defined by the end 71 of the tube 4. The instrument 1 is advanced along the osseous tunnel until images obtained from optical energy signals supplied by the waveguide 150 show that that burr 77 is in proximity to necrotic tissue or a necrotic tissue region.

Then, an irrigation supply tube (not shown), which can supply irrigant, such as water or a saline, under pressure, is attached to the leg 129 of the fitting 126. The irrigant, when supplied under pressure to the leg 129, flows from the leg 129 and into the stem 124. After entering the stem 124, the irrigant continues to flow around the waveguide 150, through the stem 124 and into and through the tube 130 and towards the burr 77. As the irrigant exiting the tube 130 at the end 134 is under pressure and confined to the open area of the osseous tunnel at the end 71 of the tube 4, when the open area becomes filled with the irrigant, the irrigant flows back toward the housing 5 through portions of the tube 4 within the inside surface 69 not occupied by the irrigant tube 130 and the thrust tube 57, as indicated by flow path B in FIG. 9. The irrigant flowing back into the tube 4 at the end 71 can include bone chip or other debris created by tissue cut by the burr 77. The irrigant supplied from the tube 130 desirably washes over the tip 152 of the waveguide 150 to maintain the tip 152 free of bone debris created during cutting of tissue by the burr 77. At the housing 5, the returning irrigant follows the flow path B through the bore 9, the pocket 11a, the pocket 12, the pocket 11b, the aperture 32 of the drive fitting 23, the bore of 33 of the fitting 23 and out the aperture 31 of the fitting 23.

A power driver unit (not shown) is then attached to the drive fitting 23 at the end 25. The driver is desirably adapted to form a water tight seal to the driver connector 8 at the end 8b, so as to provide a watertight pathway for irrigant flowing out of the aperture 31 of the drive fitting 23. When the driver unit is energized, the driver unit rotates to cause the fitting 23 to rotate about its axis. The axial rotation of the fitting 23, in turn, causes the shaft fitting 34 and the flexible shaft 38 within the thrust tube 57 to axially rotate. The rotation of the shaft 38, in turn, causes the burr 77 to rotate axially.

When the burr 77 is axially rotating and the instrument 1 is in the at rest condition, the instrument 1 can be moved by the user along the longitudinal length of the osseous tunnel to cause the burr 77 to contact and cut bone tissue at the end 71 of the tube 4 which is within the circumferential region defined by the tube 4. The irrigant supplied through the tube 130 maintains the lens tip 152 of the waveguide 150 unobstructed, by carrying away bone chips or other debris created during the cutting back to housing 5 on the flow path B extending through the tube 4.

To cut tissue outside of the circumferential region defined by the tube 4, a user operates the instrument 1 so that it is in a deflected condition. To switch the instrument 1 from the at rest condition to a deflected condition, a user depresses the lever 40 to cause the lever 40 to move at least partially toward the housing 5. When the lever 40 moves toward the housing 5, the fork 52 applies to the thrust tube 57 an axial force in the direction of the burr head portion 3. This axial force on the tube 57, in turn, causes the leaf springs 73 and 74 to begin to bend in unison away from the axis of the tube 4, which causes the burr 77 to begin to extend away from the axis of the tube 4, such that at least a portion of the burr 77 is outside the circumferential region defined by the tube 4, such as shown in FIG. 8. The high torsional stiffness of the leaf springs 73, 74 provides that the rotating burr 77 applies a sufficient lateral force to the tissue with which the burr 77 comes in contact to provide for cutting of such tissue, when the burr 77 is deflected so that a portion of the burr 77 is outside the circumferential region defined by the tube 4. The extent that the lever 40 is moved toward the housing 5 (depressed by the user) determines the extent that the burr 77 is moved away from the axis of the tube 4, and thus the radial distance from the axis of the tube 4 at which the rotating burr 77 can cut bone tissue which is outside the circumferential region defined by the tube 4. When the amount of force applied to the lever 40 is decreased, such that the extent that the lever 40 is depressed is reduced at least in part, the stored energy in the deflected springs 73, 74 causes the springs 73, 74 to begin to straighten, such that the extent to which the burr 77 is deflected away from the axis decreases. If the lever 40 is completely released by the user, such that the user no longer applies a force to the lever 40, the springs 73, 74 straighten completely and are parallel to the axis of the tube 4, and the burr 77 is completely within the circumferential region defined by the tube 4.

Therefore, a user, by controllably depressing the lever 40 and maintaining the lever 40 depressed to a desired extent, can precisely direct the burr 77 to selected regions of necrotic bone positioned outside of the circumferential region defined by the end 71 of the tube 4, and selectively remove tissue, as needed, based on viewing the necrotic region on a monitor of an endoscope using optical imaging data supplied from the waveguide 150. The close fitting relation between the osseous tunnel and the end 71 of the main tube 4 allows the instrument 1 to be precisely rotated about the axis of the osseous tunnel, thereby providing that a precise arcuate sweeping cut can be made with the burr 77 when the instrument 1 is in the deflected condition and the burr 77 is rotating. For example, the surgeon can follow the inside curvature of a cortical bone using the instrument 1.

Advantageously, the instrument of the present invention provides that a burr can be used to remove an increased volume of necrotic bone precisely, by controllably deflecting the burr to radial positions located outside of the circumferential region defined by the distal end of the instrument. The removal of necrotic bone is performed without undesired removal of healthy bone, quickly and safely, based on real-time direct visualization of the cutting. The quicker, relatively minimally invasive tissue removal technique reduces tissue morbidity, allows faster rehabilitation time and a shorter hospital stay, and can provide a more favorable and potentially successful treatment option, such as by avoiding total hip arthroplasty for treating osteonecrosis of the femoral head.

In another aspect of the invention, a surgical instrument 200 is operable for removal of bone tissue within and outside a circumferential region defined by the distal end of the instrument 200. Components in the instrument 200 which have the same construction and operation as components in the instrument 1 are referred to below using the same reference numbers as used above to describe the instrument 1.

Figure 12:
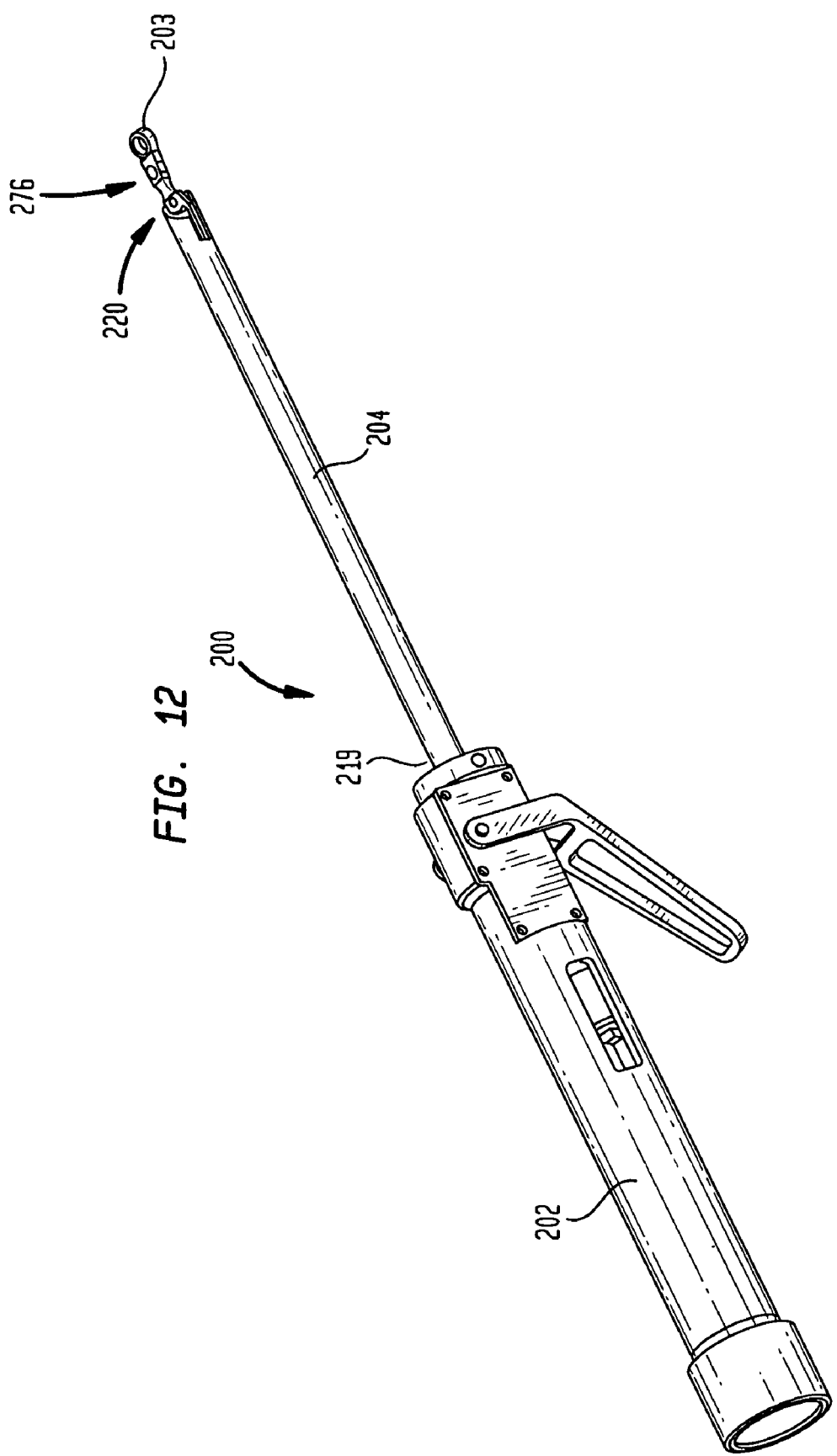
FIG. 12 is a perspective view of an exemplary surgical instrument, in accordance with another aspect of the present invention, in the at rest condition.

Referring to FIG. 12, the instrument 200 includes a main tube 204 having a handle portion 202 on a first end 219 and an articulating cutting implement portion 203 on a second end 220 opposite the first end 219.

Further referring to FIGS. 13, 14, 15, 16 and 17 and 22-23, the handle portion 202 includes a generally cylindrical housing 205, a lever 40, a hinge pin 46, a thrust fork 52, a spring guide bushing 233, a thrust collar 63, a thrust tube 258 and a cable crimper 263. The housing 205 contains a first blind bore 206 on a first end 207 for coupling with an endoscope eye piece and camera system (not shown), and a second through bore 208 on a second end 209 opposite the first end 207 for coupling with the main tube 204. The housing 205 further includes a recessed cavity 210 in proximity to the second end 209 containing a first partial wall 211a and a second partial wall 211b. The first partial wall 211a includes a first through bore 213a for slidably receiving and coupling with second outside surface 260 of the thrust tube 258, and a second through bore 214a for slidably receiving and coupling with a cable 238 and a third through bore 212a for receiving and coupling with a flexible irrigation tube 130. The second partial wall 211b includes a first through bore 213b for slidably receiving and coupling with first outside surface 259 of the thrust tube 258, and a second through bore 214b for slidably receiving and coupling with the cable 238 and a third through bore 212b for receiving and coupling with the tube 130. The bores 213a and 214a are axially aligned with the bores 213b and 214b, respectively. The bores 212a and 212b are axially offset from each other.

Figure 14:
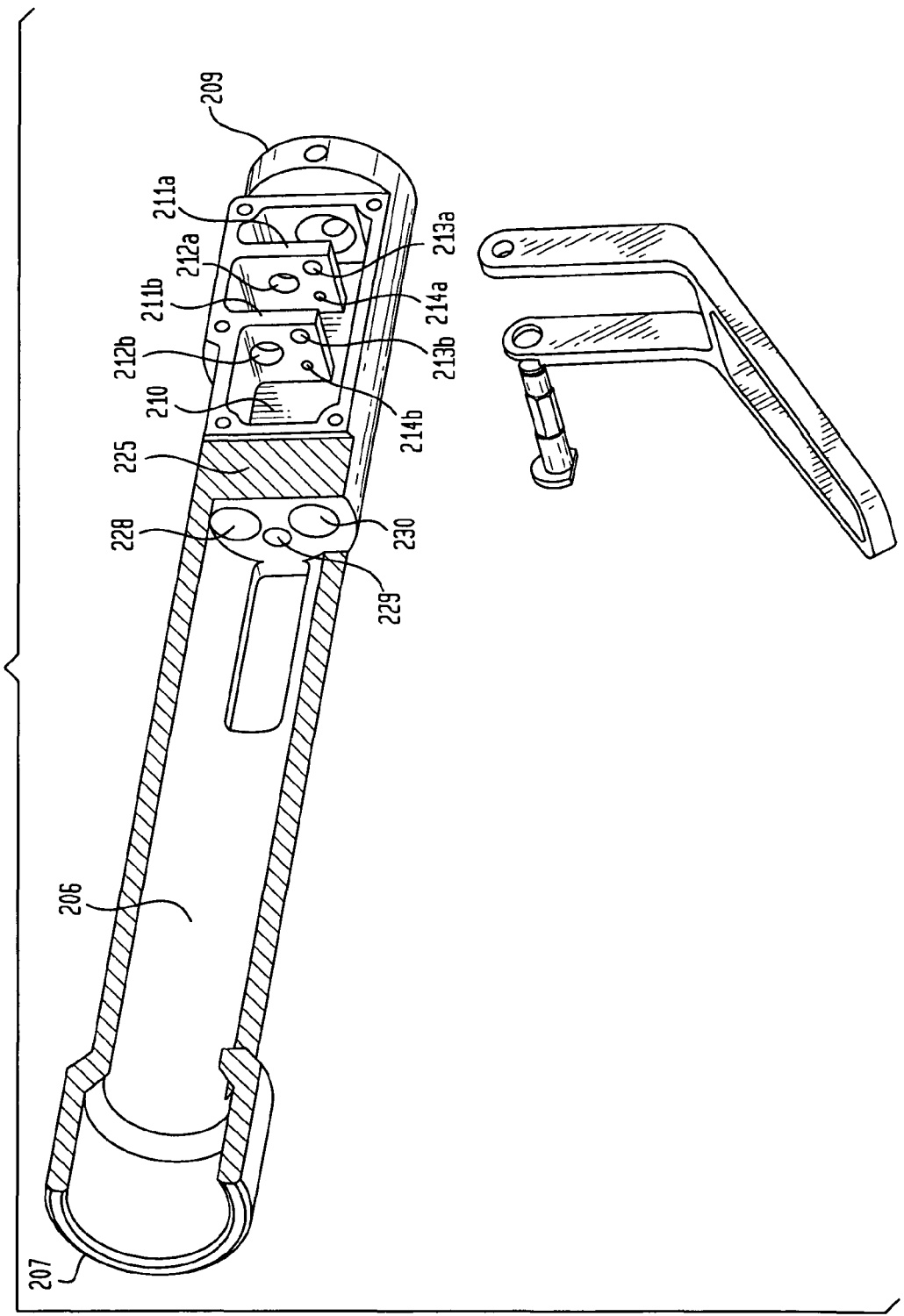
FIG. 14 is an exploded view of a portion of an exemplary handle portion of the instrument of FIG. 12.
Figure 17:
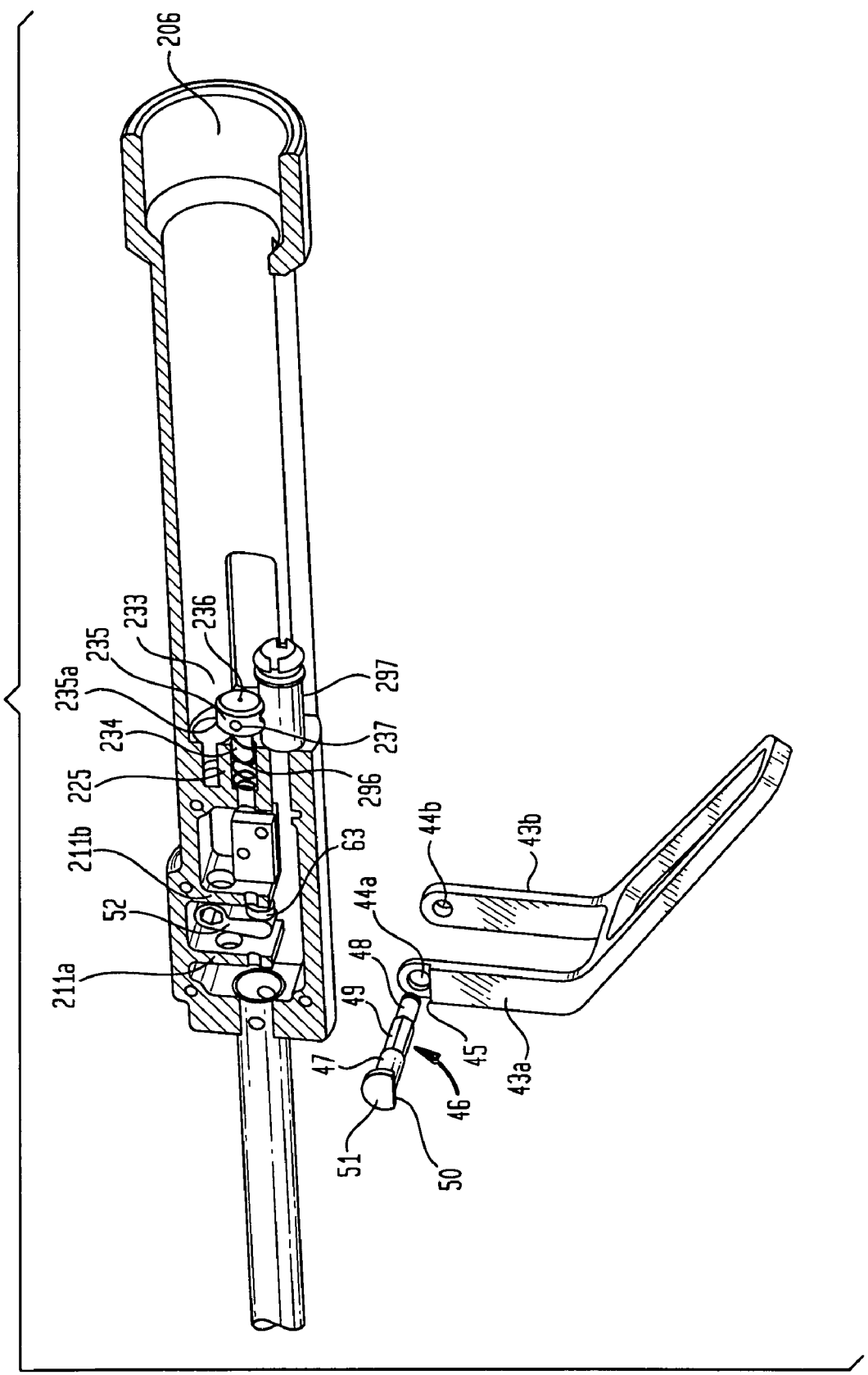
FIG. 17 is a view of a portion of the instrument of FIG. 12.

Referring to FIGS. 14 and 17, the housing 205 further includes a wall portion 225 between the recessed cavity 210 and the first bore 206, and the wall portion 225 defines a counterbore 229 in which a cable return compression spring 296 is contained. The counterbore 229 is coaxial with the bores 214a and 214b. Further referring to FIG. 22, the wall portion 225 defines a first through bore 230 for coupling with a irrigant exit port 297, and a second through bore 228 for coupling with a Y fitting 298.

Figure 13:
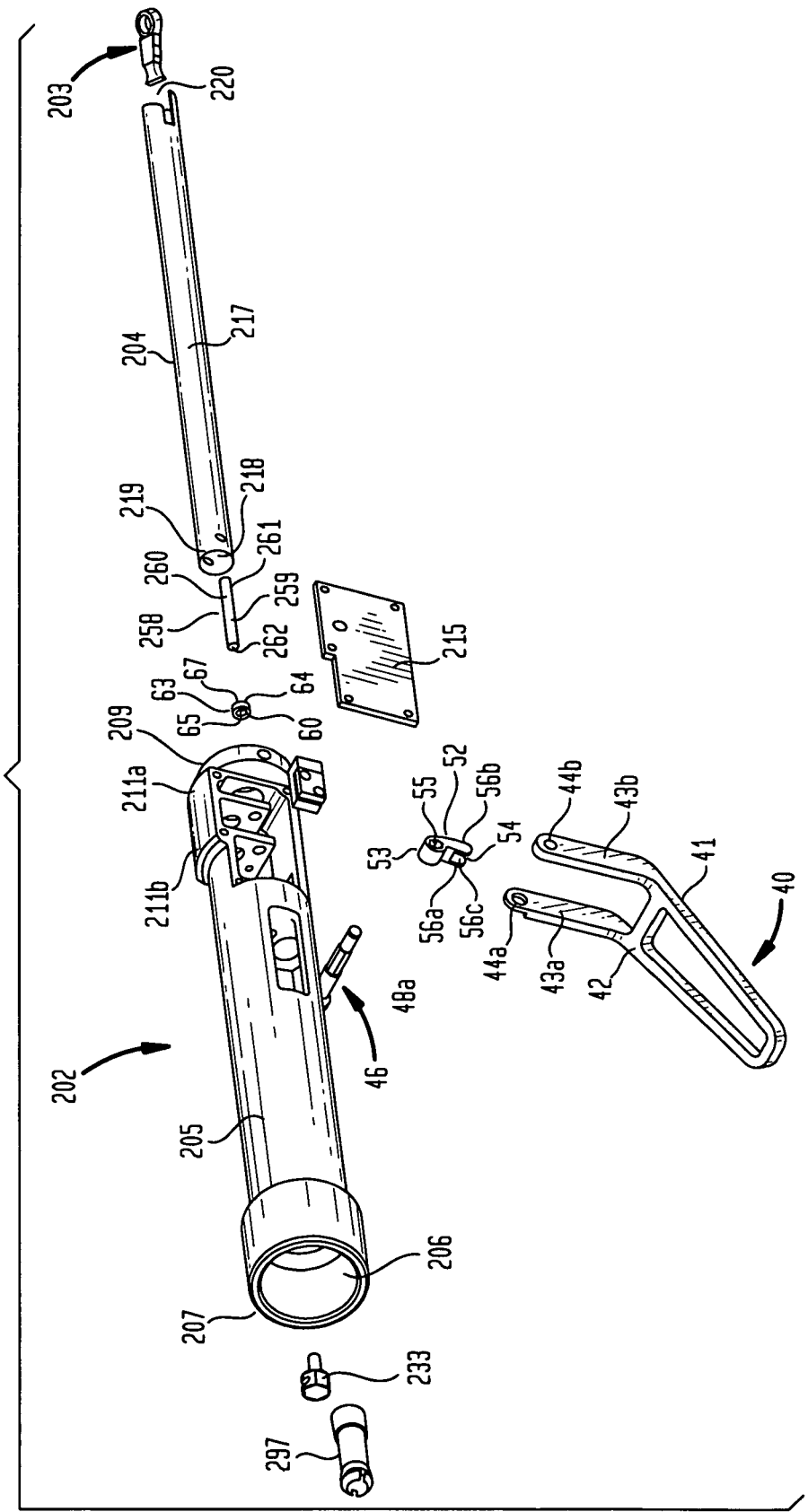
FIG. 13 is an exploded view of a portion of the surgical instrument of FIG. 12.
Figure 15:
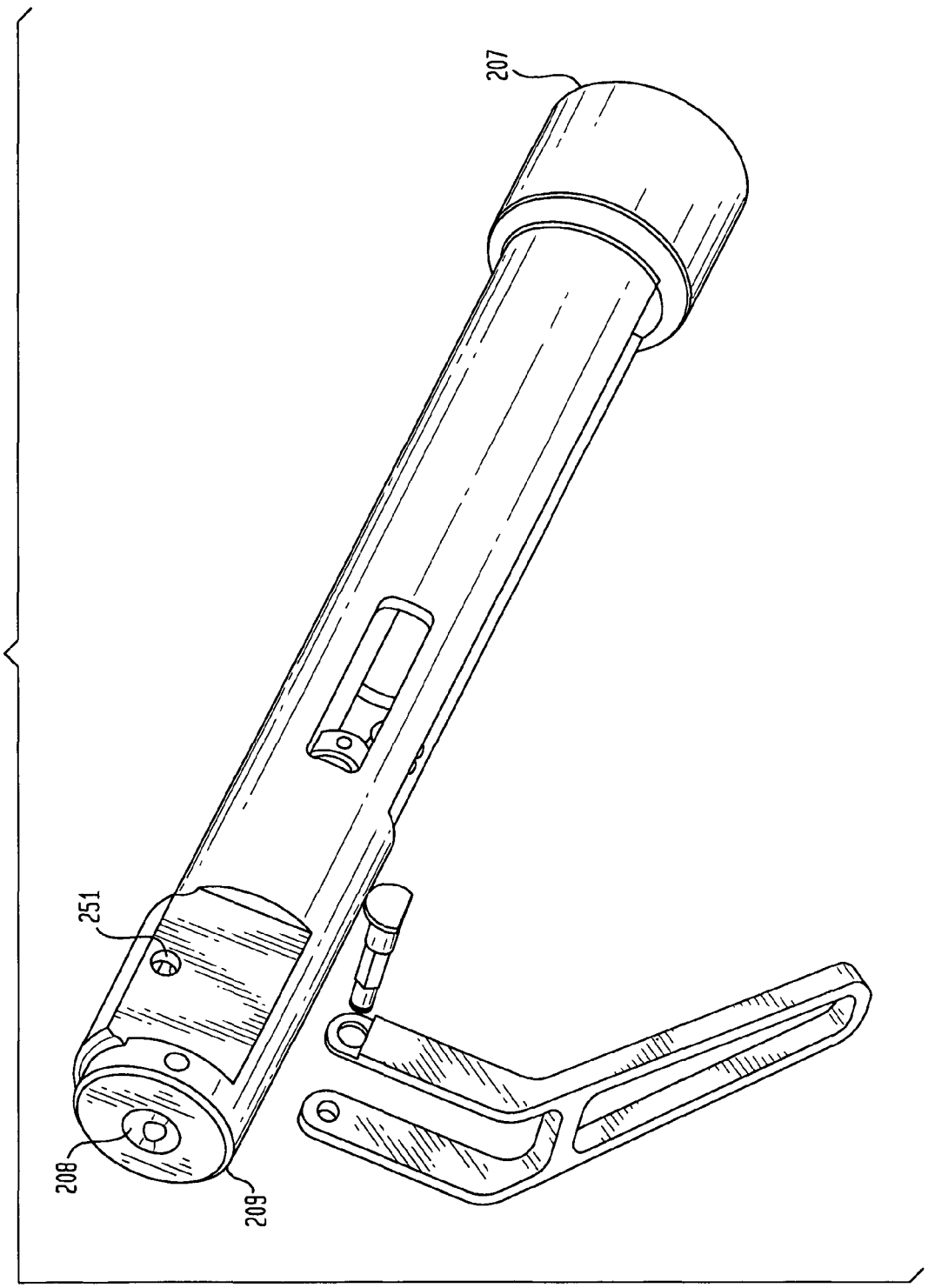
FIG. 15 is an exploded view of a portion of the handle portion of the instrument of FIG. 12.

Referring to FIGS. 13 and 15, a liquid impermeable plate 215, such as made from plexiglass, covers the recessed cavity 210 to form a water tight compartment, and defines a through bore 216 extending perpendicular to its thickness and the axis along which the tube 204 extends. The housing 205 further includes a bore 251 on the side opposite to the side of housing 205 covered by the plate 215, and the bore 251 is axially aligned with the bore 216 of the plate 215. The main tube 204 includes an outside surface 217 and an inside surface 218. The first end 219 of the tube 204 is for coupling with the second bore 208, and the second end of the tube 220 is for coupling with the articulating cutting implement portion 203.

Referring to FIG. 17, the bushing 233 has a first cylindrical portion 235 axially aligned with and extending from a second cylindrical portion 234. The second portion 234 has a smaller outer diameter than the first cylindrical portion 235, thus forming a shoulder 235a for abutting against the compression spring 296. The second cylindrical portion 234 has an outer diameter sized to provide that the outer surface of the portion 234 slidably couples with the inside diameter of the compression spring 296. The spring guide bushing 233 further contains a through hole 236 axially aligned with the first and second cylindrical portions 235, 234 and extending the entire axial length of the spring guide bushing 233. A threaded hole 237 in the first cylindrical portion 235 extends from the outer surface of the portion 235 in a direction generally perpendicular to the axis of the through hole 236 to a depth intersecting the through hole 236.

When the instrument 200 is assembled, a set screw (not shown) engages with the threaded hole 237 and firmly secures end 238b of a return cable 238 within the hole 236 of the bushing 233. In addition, the second portion 234 encircled by the spring 296 is within the bore 229, and the spring 296 abuts against the shoulder 235a of the bushing 233.

Referring to FIG. 13, the handle portion 202 further includes the lever 40, the pin 46 and the thrust fork 52. When the instrument 200 is assembled, the pin 46 extends through the bore 44a of the lever 40, the bore 251 of the housing 205, the splined bore 55 of the thrust fork 52, the bore 44b of the lever 40 and the bore 216 of the plate 215, and a nut (not shown) is threaded to the threaded end of the pin 46 extending through the bore 216. The hinge pin 46, thus, forms a rotating hinged connection between the lever 40 and the body 205, and the pin 46 cannot rotate with respect to the lever 40. In addition, the hinge pin 46 is mated with the thrust fork 52, such that the hinge pin 46 does not rotate with respect to the fork 52. As discussed below, rotation of the lever 40 towards the body 205, by depressing the lever 40, controls the extent that the cutting implement portion 203 is deflected away from the axis of the tube 204 and positioned outside the circumferential region defined by the end 220 of the tube 204.

Referring to FIG. 13, the housing 205 contains a thrust assembly comprising the thrust tube 258 and the thrust collar 63. The tube 258 has a first cylindrical portion 259 and a second cylindrical portion 260, which extends from and is coaxial with the portion 259. The outside diameter of the first portion 259 exceeds the outside diameter of the second portion 260, and a shoulder 261 is formed at the junction of the portions 259, 260. The tube 258 has an inside surface 262 having a diameter 262A extending its entire length. The second portion 260 extends through and is coupled to the bore 213a, and the first portion 259 extends through and is coupled to the bore 213b.

Figure 23:
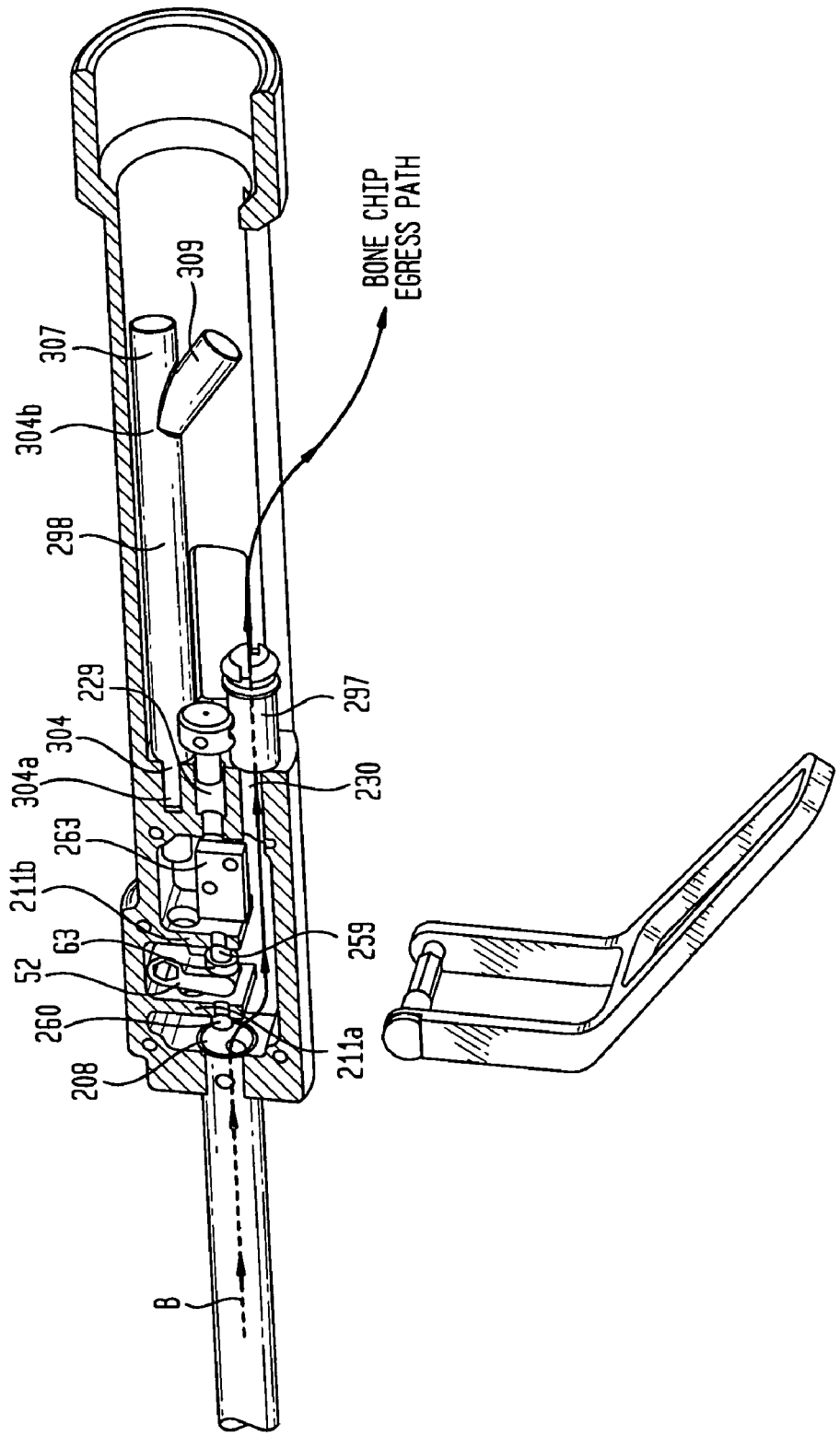
FIG. 23 is a side view of a portion of the handle portion of the instrument of FIG. 12.

Referring to FIGS. 13 and 23, the first face 66 of the thrust collar 63 is sized for coupling against the shoulder 261 of the thrust tube 258, and the second face 67 is sized for coupling with the first and second tabs 56a and 56b of the thrust fork 52. The inside surface 65 of the thrust collar 63 has a diameter sized for receiving therethrough and coupling with the outside surface of the portion 260 of the thrust tube 258. The outside diameter of the surface 64 of the thrust collar 63 is larger than the width of the slot 56c formed between the first tab 56a and the second tab 56b of the thrust fork 52. When the instrument 200 is assembled, the portion 260 of the tube 258 is received in the slot 56c and the second face 67 of the collar 63 abuts against the tabs 56a, 56b.

Figure 16:
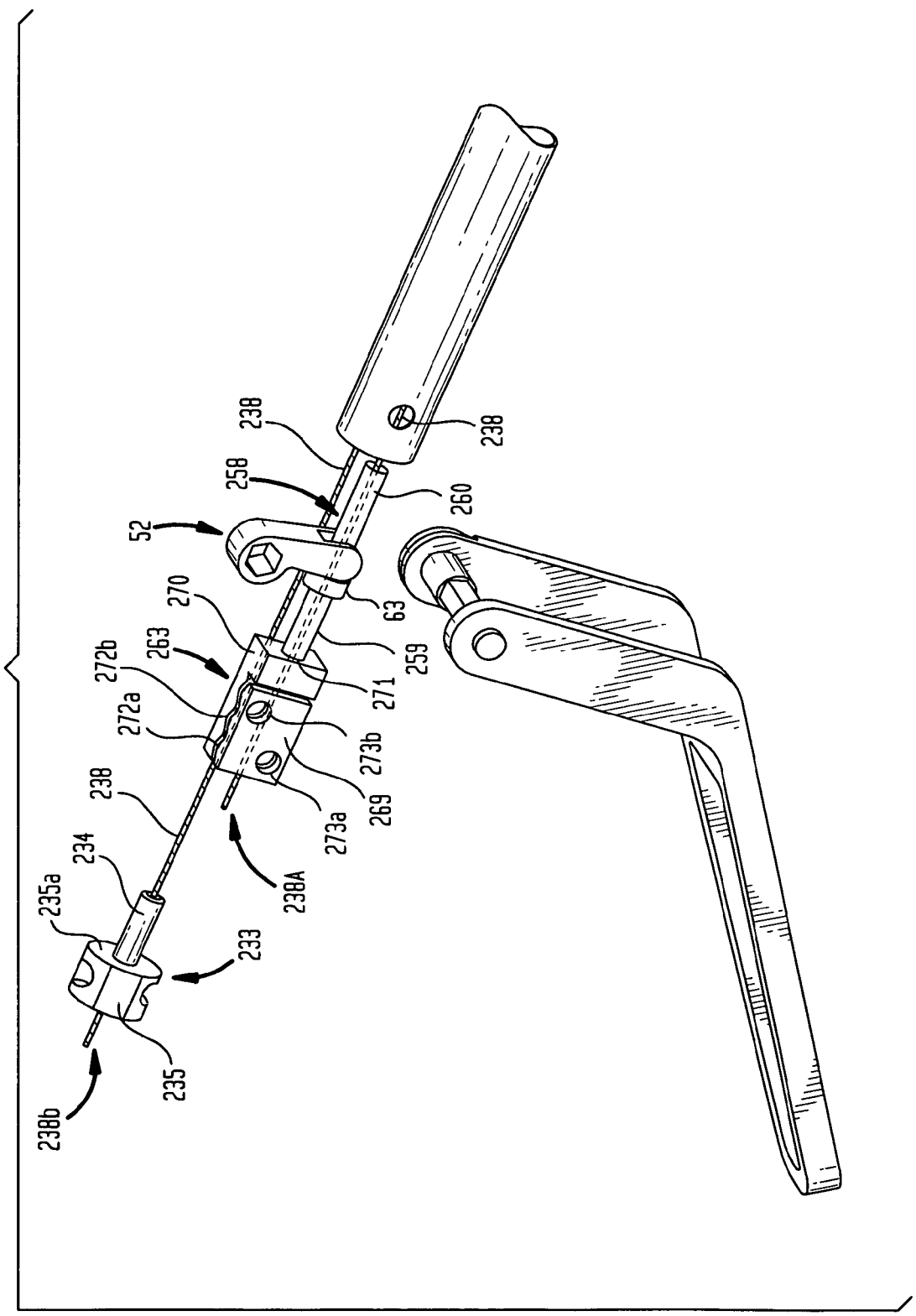
FIG. 16 is a view of a portion of the instrument of FIG. 12.

Referring to FIG. 16, the cable crimper 263 contains a first portion 269 with a first through hole 273a and a second through hole 273b, and a second portion 270 with two threaded holes coaxially aligned with the first through hole 273a and second through hole 273b, respectively, of the first portion 269. The second portion 270 further contains a counterbore 271 generally perpendicular to the holes 273a, 273b for receiving and coupling with the outside surface of the portion 259 of the thrust tube 258. Two set screws (not shown) are inserted through the first through hole 273a and the second through hole 273b, respectively, and engaged with threaded holes on the second portion 270, thus allowing the first and second portions 269 and 270 to be tightened to each other. Abutting surfaces 272a and 272b of the first and second portions 269 and 270, respectively, are mutually textured for interlocking an end portion 238a of the cable 238 therebetween.

Figure 18:
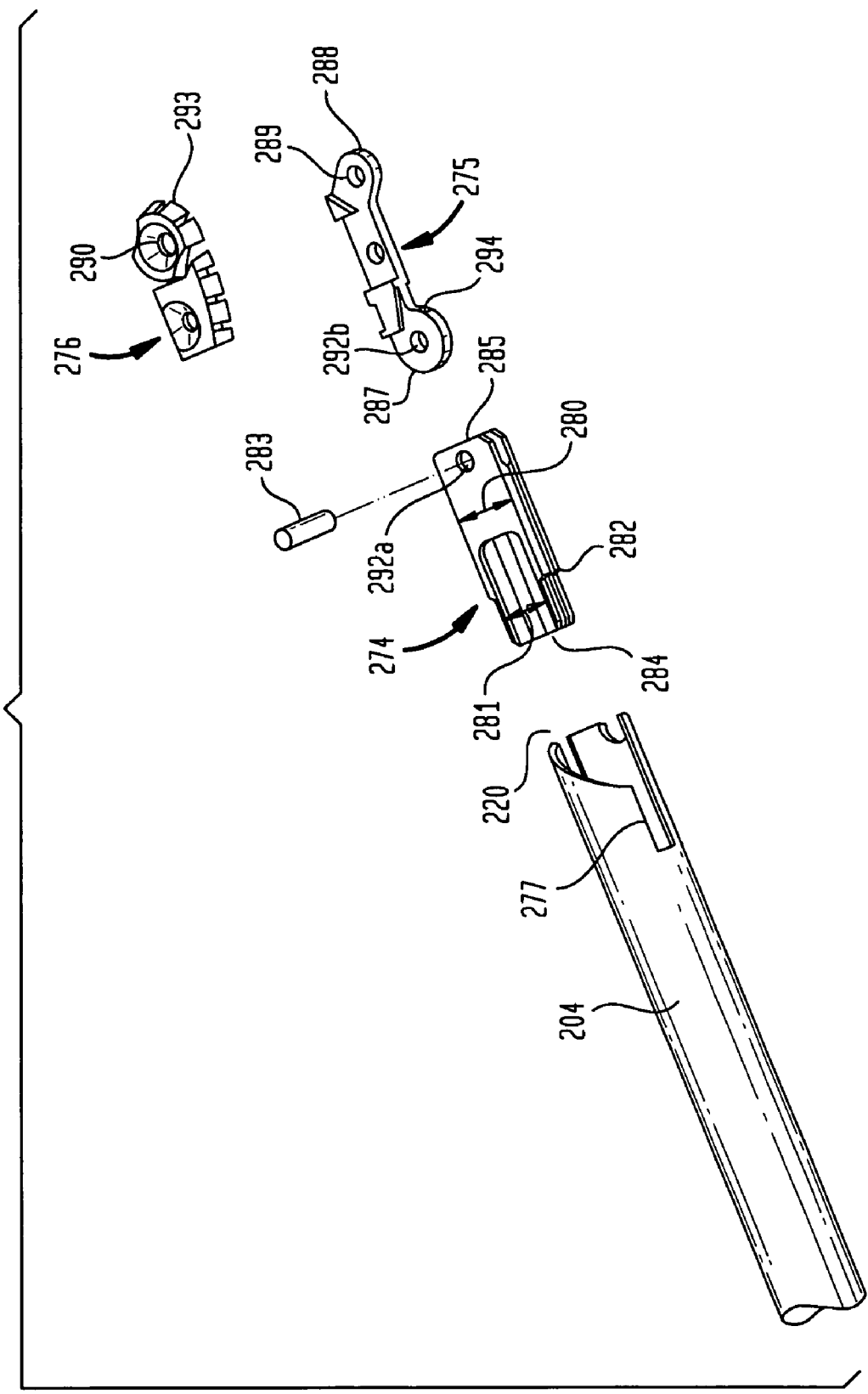
FIG. 18 is an exploded view of an exemplary cutting implement of the instrument of FIG. 12.
Figure 19:
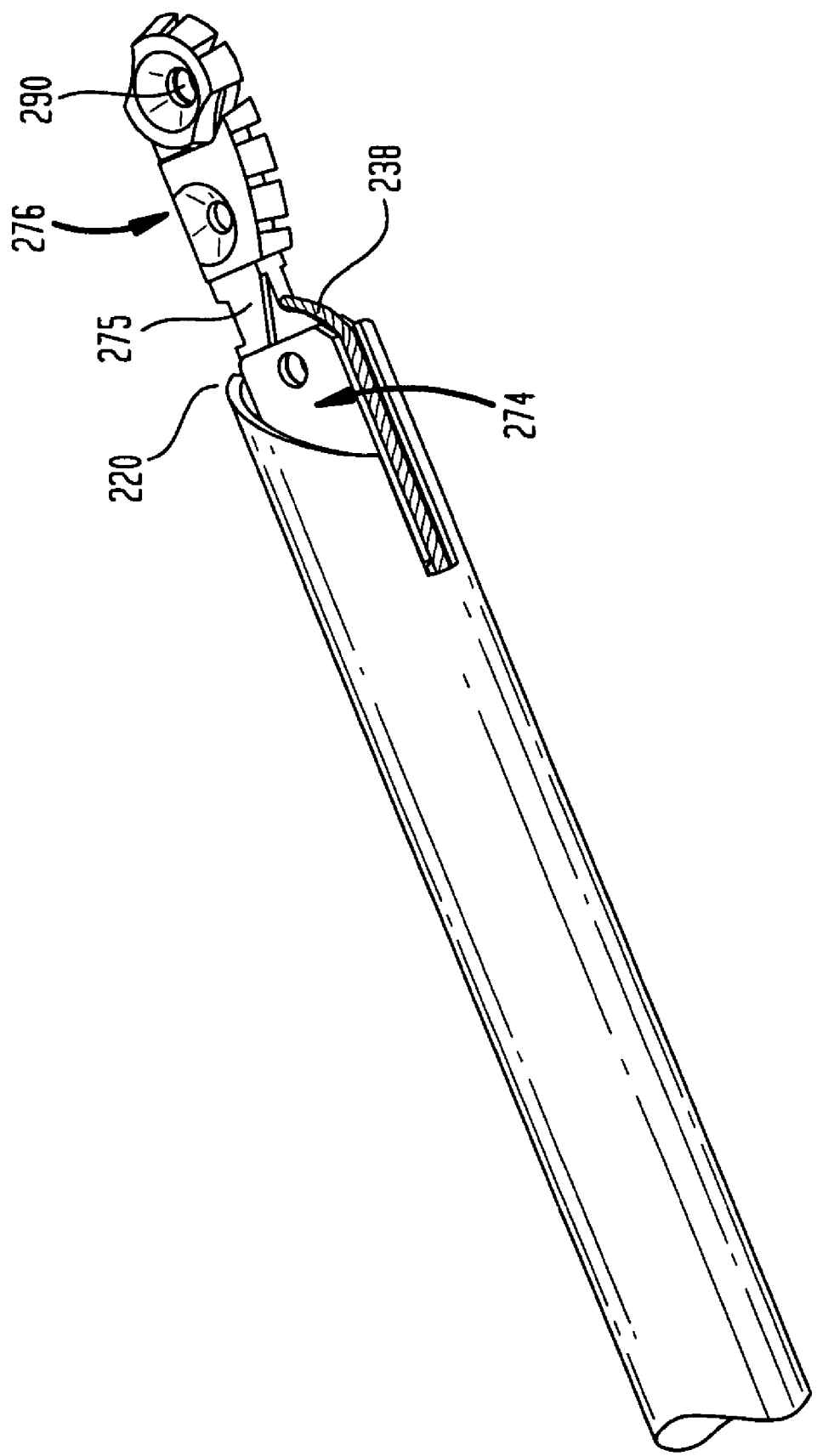
FIG. 19 is a perspective view of the cutting implement of the instrument of FIG. 12 in the at rest condition.
Figure 20:
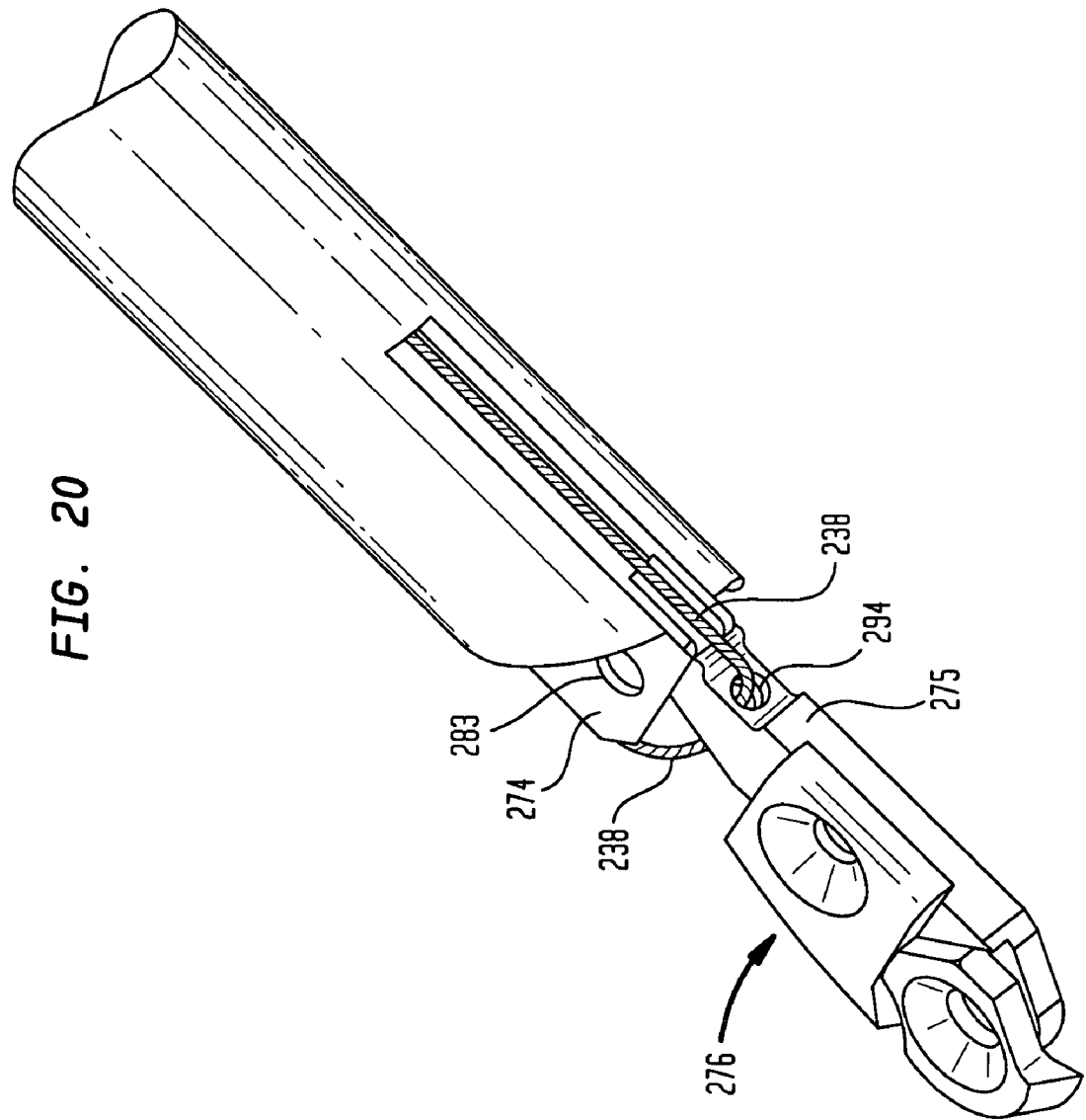
FIG. 20 is another perspective view of the cutting implement of the instrument of FIG. 12 in the at rest condition.

FIGS. 18, 19 and 20 show the articulating cutting implement portion 203. The cutting portion 203 includes a cutter support housing 274, an articulating arm 275 and a cutting implement 276. The cutter support housing 274 includes a first end 284 for coupling with a slot 277 at the second end 220 of the main tube 204, and a second end 285 opposite the first end 284 which includes a slot 286 for coupling with the articulating arm 275. The second end 285 of the cutter support housing 274 further includes a through bore 292a oriented perpendicular to the slot 286. The cutter support housing 274 has a first width 280 which matches the outside diameter of the main tube 204, and a second smaller width 281 which matches the inside diameter of the main tube 204. A shoulder 282 formed at the junction of the width 280 and the width 281 portions of the housing 274 serves as an abutting surface against the wall of the main tube 204 when the housing 274 is coupled to the tube 204 at the slot 277.

Still referring to FIG. 18, the articulating arm 275 includes a first end 287 for coupling with the slot 286 of the cutter support housing 274 and a second end 288 opposite the first end 287 for coupling with the cutting implement 276. The first end 287 of the articulating arm 275 further includes a bore 292b. The second end 288 of the articulating arm 275 further includes a bore 289 for coupling with the cutting implement 276. The cutter support housing 274 and the articulating arm 275 are rotatably coupled when a pivot pin 283 is inserted into and through the bores 292a and 292b.

The cutting implement 276 includes a through bore 290 for coupling with the articulating arm 275 using a screw (not shown) inserted through the bore 290 and the bore 289. In addition, the cutting implement 276 includes a series of outwardly projecting tabs 293 ground in such a manner as to form sharp cutting surfaces. The cutting implement 276 can be fabricated from two pieces (as shown), or alternatively one piece. The first end 287 of the articulating arm 275 further contains a through bore 294 for coupling with and through which the cable 238 is received. When the instrument 200 is assembled, the articulating arm 275 may be staked or crimped in the region of the bore 294 to prevent slippage of the cable 238 through the bore 294 when an axial force is applied to the cable 238. As discussed below, during operation of the instrument 200, an axial force is applied to the cable 238, which results in the cable 238 transmitting torque to the articulating arm 275, thereby forcing rotation of the arm 275 with the cutting implement 276 away from the axis of the tube 204.

Figure 22:
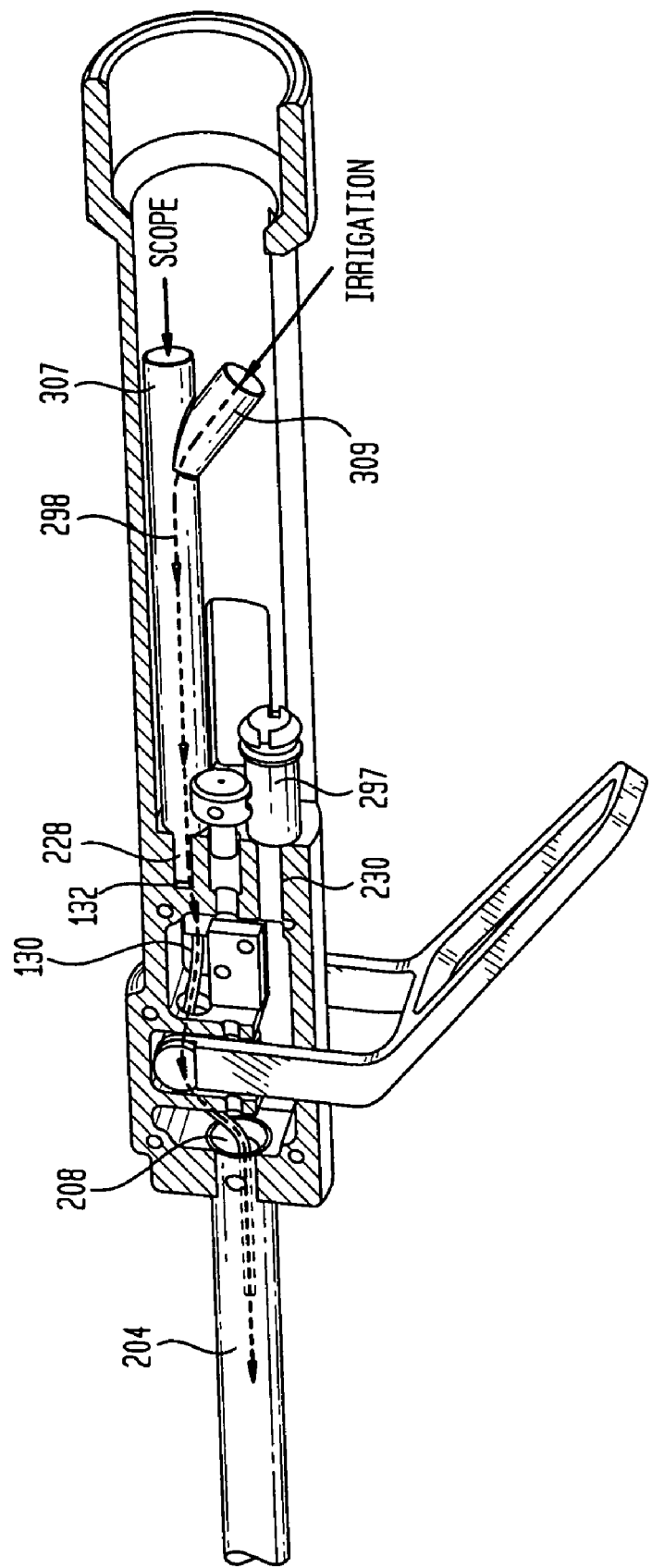
FIG. 22 is a side view of a portion of the handle portion of the instrument of FIG. 12.

Referring again to FIG. 14, and also to FIGS. 22, 23 and 24, stem 304 of the Y fitting 298 is received with the bore 228 of the main housing 205. The Y fitting 298 further includes legs 307 and 309 which join at an end 304b of the stem 304. A flexible tube 130 at end 132 is connected to end 304a of the stem 304, which is opposite to the end 304b, to form a watertight seal. The tube 130 has an outer diameter sized so that the tube 130 can extend through the bores 212a, 212b, the bore 208 and then into and through the tube 204. The tube 130 extends through the tube 204 and terminates adjacent the end 285 of the cutter support housing 274. The tube 130 has a sufficiently large inner diameter for receiving therethrough a fiber optic waveguide 150.

When the instrument 200 is assembled, the cable 238, from the end 238b, extends from the spring guide bushing 233, through the bore 229 and the bores 214b, 214a, through the bore 208 and out of the housing 205 into the tube 204. The cable 238 then further extends through the tube 204 to the end 220 and at the end 220 emerges from the tube 204 on the side of the cutting implement portion 203 opposite to the tabs 293. The cable 238 then extends through the bore 294 and then back into the tube 204 at the end 220. The cable 238 then extends through the tube 204, the bore 208 of the housing 205 and the thrust tube 258, and is clamped at the end 238a in the crimper 263. Further, the tabs 56a, 56b of the thrust fork 52 are coupled to the portion 259 of the tube 258 and disposed between the thrust collar 63 and the wall 211a, with the tabs 56a, 56b abutting against the collar 63.

In addition, the cable 238 is of a length and the compression spring 296 is sized and has a resiliency such that, when the instrument 200 is in the at rest condition (the lever 40 is not depressed), the spring bushing 233 is spaced from the facing portion of the wall 225, the crimper 263 abuts against the wall 211b, the portion 259 of the thrust tube 258 extending away from the wall 211b toward the end 207 is received completely within the bore 271 so as to abut against the crimper 263, a portion of the tube portion 259 is disposed between the collar 63 and the wall portion 211b, and the tabs 56a, 56b abut against the wall portion 211a. Further, in the at rest condition of the instrument, the cutting implement portion 203 is aligned with the axis of the tube 204 and within the circumferential region defined by the end 220 of the tube 204.

When the lever 40 is depressed to set the instrument 200 to a deflected condition, the lever 40 rotates towards the housing 205, which causes the end 54 of the thrust fork 52 to rotate away from the wall portion 211a, which in turn causes the tabs 56a, 56b to apply an axial force in the direction of the end 207 of the housing 205 at the thrust collar 63. The creation of such axial force results in the portion 260 of the tube 258 forcing the crimper 263 away from the wall portion 211b and the bushing 233 being axially pulled in the direction of the cutting implement portion 203, thereby compressing the compression spring 296. Further, the axial force that is created causes the cable 238 at the bore 294 to apply a force upon the articulating arm 275, such that the arm 275, with the attached cutting implement 276, rotates about a pivot point P which is coaxial with the pivot pin 283. The rotation of the implement 276 about the pivot point P results in the implement 276 moving away from the axis of the tube 204, such that the implement 276 extends outside the circumferential region defined by the tube 204. Upon release of the lever 40, such that the lever 40 is no longer depressed or still partially depressed, the spring 296 decompresses. The decompression of the spring 296 forces the bushing 233 towards the end 207 of the housing 202, which causes the end 238b of the cable 238 to move toward the end 207 and results in the cutting implement 276 moving toward the axis of the tube 204.

A surgical procedure can be performed with the instrument 200, such as to remove necrotic tissue from the femoral bone as part of a core decompression procedure, as follows. Similarly as described above for performing a surgical procedure with the instrument 1, an osseus tunnel may be initially created whose diameter substantially matches the outside diameter of the tube 204 at the end 220, which defines a circumferential region at the end 220 of the tube 204. A waveguide 150 is then inserted through the leg 307 of the fitting 298 and then advanced through the fitting 298 and the tube 130 until the tip 152 of the waveguide 150 is adjacent the end 285 of the cutting support housing 274. The other end of the waveguide 150 is connected to a suitable direct imaging apparatus, similarly as described above for the instrument 1.

After the waveguide 150 has been positioned within the tube 130, the instrument 200 is introduced into the osseous tunnel by first inserting the articulating cutting implement portion 203, followed by the tube 204 into the tunnel. When the instrument 200 is initially introduced into the tunnel, the lever 40 is not depressed such that the instrument 200 is in the at rest condition. In the at rest condition of the instrument 200, the cutting implement 276 is straight and parallel to the axis of the tube 204 and, thus, does not extend away from the axis of the tube 204 and is completely within the circumferential region defined by end 220 of the tube 204.

Based on image data provided by the waveguide 150, the user advances the instrument 200 into the osseous tunnel until the cutting implement 276 is in close proximity to necrotic tissue or a necrotic tissue region. Then, an irrigation tube (not shown) which can supply irrigant, such as water or a saline, under a controlled pressure, is attached to the leg 309. The irrigant under pressure flows through the leg 309, the stem of the Y fitting 298, into and through the tube 130 and exits at the end 130b of the tube 130 (not shown) at the cutter support housing 274. Similarly as described above for the instrument 1, after the irrigant fills the open space in the tunnel at the end 220 of the tube 204, the irrigant flows back through the tube 204. The return flow of fluid emerges from the tube 204 and enters the recessed cavity 210 of the housing 205 through the bore 208, and exits the cavity 210 through the bore 230 and the irrigant exit port 297. The irrigant exit port 297 is suitably coupled to a tube extending from a conventional aspirator (not shown).

After insertion of the instrument 200 into the tunnel while the instrument 200 is in the at rest condition, the instrument 200 can be positioned so that the cutting implement 276 contacts tissue within the circumferential region defined by the tube 204. Then, by rotating the instrument 200 about its axis, any tissue coming in contact with the most distal projections 293 of the cutting implement 276 is cut. While the instrument 200 remains in the at rest condition, the cutting of tissue can occur only within the circumferential region defined by the tube 204.

Figure 21:
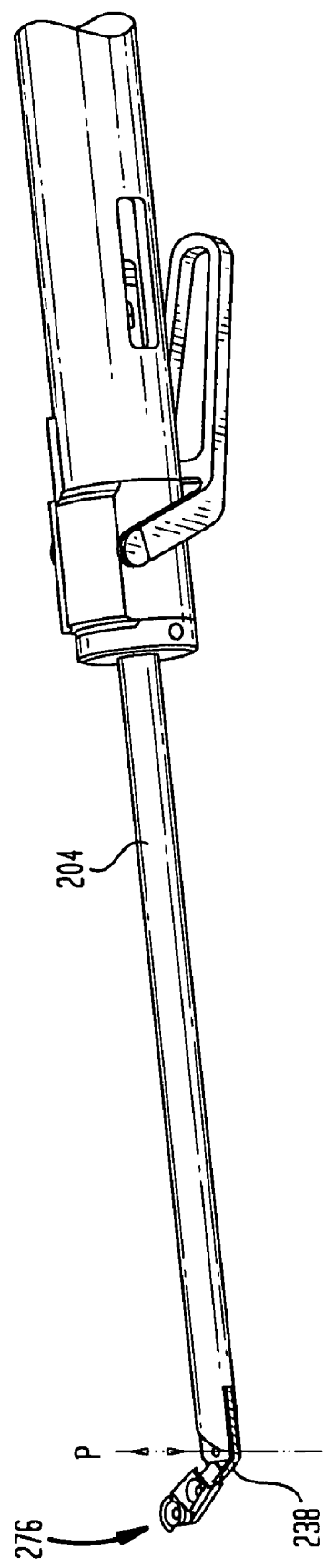
FIG. 21 is a perspective view of the instrument of FIG. 12 in a deflected condition.

To provide that tissue outside the circumferential region of the tube 204 can be cut, the instrument 200 needs to be in the deflected condition. When the instrument 200 is in the at rest condition, the deflected condition of the instrument 200 is attained by depressing the lever 40, which causes the lever 40 to rotate toward the housing 205. When the lever 40 is depressed, the fork 52 forces the tube 58 axially in the direction of the end 207 of the handle portion 202, which in turn creates an axial force on the end 238a of the cable 238 in the direction of the end 207 of the handle portion 202. This axial force, in turn, causes the articulating arm 275, to which the cutting implement 276 is coupled, to rotate about the pivot axis P at the pin 283, which results in the cutting implement 276 moving away from the axis of the tube 204 and being disposed outside the circumferential region defined at the end 220 of the tube 204, such as shown in FIG. 21. As the cutting implement 276 moves away from the axis of the tube 204 and extends further away from the circumferential region defined by the tube 204, the projections 293 dig into the bone in the wall of the osseous tunnel. The surgeon then rotates the instrument 200 back and forth about the axis of the tube 204 to scrape away the undesired bone outside the circumferential region defined by the tube 204. The extent that the lever 40 is depressed determines the extent that the cutting implement 276 can extend away from the axis of the tube 204 and, therefore, the radial distance from the axis of the tube 204 at which scraping of bone can be performed.

Thus, by controlled depressing and releasing of the lever 40 and viewing of images of the distal end of the tunnel supplied by the waveguide 150, a surgeon can precisely direct the cutting implement 276 to selected regions of necrotic bone outside the circumferential region defined at the end 220 of the tube 204. As in the instrument 1, the irrigant flowing through the tube 130 in the instrument 200 washes over the lens or tip 152 of the waveguide 150 to maintain the lens free of bone debris created by the scraping of tissue with the projections 293 of the cutting implement 276.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A surgical instrument comprising:
    a tubular member having an axis, a first end coupled to a drive housing and a second end coupled to a cutting apparatus including a rotatable and deflectable cutting element, wherein the second end of the tubular member defines a circumferential region;
    a drive shaft having a first end coupled to a rotatable drive member in the housing and a second end coupled to the cutting element, wherein the drive shaft translates rotational motion at the drive member to the cutting element to cause rotation of the cutting element;
    a thrust member having a first end within the housing and a second end coupled to a resilient member in the cutting apparatus, wherein the resilient member is coupled to the cutting element and bending of the resilient member causes movement of the cutting element away from the axis of the tubular member;
    a first fluid flow path extending from within the housing, through a bore defined in the tubular member, and terminating at the cutting apparatus;
    wherein the bore of the tubular member includes a second fluid flow path extending between the drive housing and the cutting apparatus and being distinct from the first flow path;
    wherein, in an at rest condition of the instrument, the cutting element is disposed within the circumferential region defined by the second end of the tubular member;
    wherein the first flow path or the second flow path is for receiving an optical waveguide having a lens tip positionable proximate the cutting apparatus; and
    a moveable member coupled to the first end of the thrust member and operable to set the instrument to a deflected condition, wherein when the instrument is in the deflected condition the moveable member applies a force at the first end of the thrust member causing the second end of the thrust member to bend the resilient member, such that the cutting element is moved away from the axis of the tubular member and is disposed at least partially outside the circumferential region defined by the second end of the tubular member, wherein, in the deflected condition of the instrument, an extent the cutting element is disposed outside the circumferential region is in accordance with an extent the thrust member is caused to move toward the cutting element by movement of the moveable member.

2. The surgical instrument of claim 1, wherein the moveable member includes a lever rotatably coupled to the housing, wherein when the lever rotates towards the housing the cutting element moves away from the tubular axis, and wherein when the lever rotates away from the housing the cutting element moves toward the tubular axis.

3. The surgical instrument of claim 2, wherein the resilient member biases the cutting element toward the axis of the tubular member such that the extent that the cutting element is moved away from the tubular axis depends on an amount of force applied to the lever to cause rotation of the lever toward the housing.

4. The surgical instrument of claim 1, wherein the resilient member includes first and second leaf springs coupled to each other and to the cutting element, wherein the second leaf spring is fixed to the tubular member, wherein the first and second leaf springs are flat and parallel when the instrument is in the at rest condition and wherein, when a force is applied to the first end of the thrust member, the first leaf spring moves in relation to the second spring to cause bending of the first and second leaf springs away from the tubular axis such that the cutting element is moved away from the axis of the tubular member.

5. The surgical instrument of claim 4, wherein the first and second leaf springs have a torsional stiffness sufficient to provide for cutting of tissue based on contact between the cutting element and the tissue when the instrument is in the deflected condition and the cutting element is rotating.

6. The surgical instrument of claim 1, wherein the thrust member defines a bore through which the drive shaft extends.

7. The surgical instrument of claim 1, wherein the drive member includes a shaft fitting for transmitting torque applied to the drive member to the first end of the drive shaft.

* * * * *